(12) United States Patent
Miyoshi et al.

(10) Patent No.: US 8,795,200 B2
(45) Date of Patent: Aug. 5, 2014

(54) PIERCING DEVICE AND BLOOD INSPECTION DEVICE

(75) Inventors: Koji Miyoshi, Ehime (JP); Takeshi Nishida, Fukuoka (JP); Yoshinori Amano, Ehime (JP); Toshiki Matsumoto, Ehime (JP); Masataka Nadaoka, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 783 days.

(21) Appl. No.: 12/670,950

(22) PCT Filed: Jul. 31, 2008

(86) PCT No.: PCT/JP2008/002061
§ 371 (c)(1),
(2), (4) Date: Jan. 27, 2010

(87) PCT Pub. No.: WO2009/016844
PCT Pub. Date: Feb. 5, 2009

(65) Prior Publication Data
US 2010/0191147 A1    Jul. 29, 2010

(30) Foreign Application Priority Data

Jul. 31, 2007  (JP) .................................. 2007-198375

(51) Int. Cl.
| A61B 5/00 | (2006.01) |
| A61B 17/32 | (2006.01) |
| A61B 17/14 | (2006.01) |
| A61B 5/15 | (2006.01) |
| A61B 5/145 | (2006.01) |
| A61B 5/1486 | (2006.01) |

(52) U.S. Cl.
CPC ........... *A61B 5/1411* (2013.01); *A61B 5/14535* (2013.01); *A61B 5/1486* (2013.01); *A61B 5/14532* (2013.01)
USPC ............................ 600/583; 606/167; 606/181

(58) Field of Classification Search
USPC .......... 600/583; 606/9, 167, 181, 182; 607/89
See application file for complete search history.

(56) References Cited

U.S. PATENT DOCUMENTS 6,733,493 B2 *  5/2004  Gruzdev et al. .................... 606/9
7,510,564 B2 *  3/2009  Mace ............................. 606/181

(Continued)

FOREIGN PATENT DOCUMENTS

| JP | 10-501992 | 2/1998 |
| JP | 2000-152923 | 6/2000 |
| JP | 2004-97603 | 4/2004 |
| WO | 94/09713 | 5/1994 |

*Primary Examiner* — Devin Henson
(74) *Attorney, Agent, or Firm* — Greenblum & Bernstein, P.L.C.

(57) ABSTRACT

A puncturing apparatus includes a housing having a first case and a second case, the housing configured to move at least one of the first case and the second case so that the cases are in an overlapping state in which the first case and the second case overlap one another or a non-overlapping state. A puncturer is housed in the housing and a puncture starting mechanism, having a puncturing button, is configured to activate the puncturer. A first safety section is configured to prevent at least one of the puncturing opening and the puncturing button from being exposed, by placing the first case and the second case in the overlapping state, and a second safety section is configured to disable operation of the puncture starting mechanism in the non-overlapping state of the first case and the second case.

21 Claims, 23 Drawing Sheets

(56) References Cited

U.S. PATENT DOCUMENTS

| | | | |
|---|---|---|---|
| 7,582,063 B2 * | 9/2009 | Wurster et al. | 600/584 |
| 8,012,103 B2 * | 9/2011 | Escutia et al. | 600/583 |
| 8,062,235 B2 * | 11/2011 | Planman et al. | 600/584 |
| 2007/0067119 A1 * | 3/2007 | Loewen et al. | 702/57 |
| 2009/0163944 A1 | 6/2009 | Nagao et al. | |
| 2010/0030037 A1 | 2/2010 | Matsumoto et al. | |
| 2010/0042016 A1 | 2/2010 | Akiyama | |

* cited by examiner

PIERCING DEVICE AND BLOOD INSPECTION DEVICE

TECHNICAL FIELD

The present invention relates to a puncturing apparatus that punctures skin and so forth and a blood test apparatus using the puncturing apparatus.

For example, conventionally, a conventional puncturing apparatus described in patent document 1 has been known.

FIG. 1 is a block diagram showing the configuration of the puncturing apparatus described in patent document 1.

In FIG. 1, puncturing apparatus 8 has a configuration including: housing 1; control section 2 provided in housing 1; puncturing button 3 connected to control section 2 and exposing from housing 1; battery 4 that supplies power to control section 2; switch 5 connected to control section 2, which is a safety means; laser emitting device 6 connected to control section 2, which is a puncturing means; and puncturing opening 7 provided in housing 1, where laser light 6a outputted from laser emitting device 6 penetrates.

The operation of the above-described puncturing apparatus 8 will be described.

Skin of the patient (not shown) touches puncturing opening 7 provided in puncturing apparatus 8. Then, puncturing button 3 is pressed after switch 5 is operated to release the safety means. The signal indicating that button 3 is pressed is identified by control section 2, and control section 2 activates laser emitting device 6. Laser emitting device 6 emits laser light 6a, and this emitted laser light 6a penetrates puncturing opening 7 and punctures the skin of the patient. A small amount of blood (not shown) exudes from the punctured skin. For example, blood sugar level and so forth is tested using the blood exuding from the skin.

Puncturing apparatus 8 poses a risk of emitting laser light 6a by accident, and therefore the following measures are taken to avoid such risk. That is, switch 5 as a safety means is provided in order not to press puncturing button 3 by accident. Here, even if puncturing button 3 is pressed, laser emitting device 6 does not emit laser light 6a until switch 5 is operated.
Patent Document 1: Published Japanese Translation of PCT Patent Application No. 10-501992

DISCLOSURE OF INVENTION

Problems to be Solved by the Invention

However, since such conventional puncturing apparatus has such a configuration that switch 5 as a safety means can be touched on the surface of housing 1, it is possible to release the safety means by touching switch 5 erroneously during some activities and so forth. In this case, since puncturing button 3 is exposed from housing 1, it is possible to be pressed erroneously due to an impact when the apparatus falls for example. If puncturing button 3 is pressed, laser emitting device 6 emits laser light 6a erroneously because the safety means has been already released, and this causes safety issues.

The present invention solves the above-mentioned problems. It is therefore an object of the present invention is to provide a puncturing apparatus and a blood test apparatus that can more improve safety.

Means for Solving the Problem

The puncturing apparatus according to the present invention has a configuration including: a housing that is movable to place a first case and second case in an overlapping state in which the first case and the second case overlap one another and a non-overlapping state; a puncturing section that is housed in the housing and that performs puncturing through an puncturing opening; a puncturing starting mechanism that activates the puncturing section; a first safety section that prevents at least one or more of the puncturing opening and a puncturing button from being exposed, by placing the first case and the second case in the overlapping state of; and a second safety section that disables operation of the puncturing starting mechanism in the non-overlapping state of the first case and the second case.

The blood test apparatus according to the present invention has a puncturing apparatus that punctures the skin and tests components of blood exuding from skin by puncturing. A puncturing apparatus described above is used as the puncturing apparatus.

Advantageous Effects of Invention

The present invention has a first safety means that places a first case and a second case in a state in which the first case and the second case are placed in the overlapping state one another, and a second safety means that disables a puncturing starting mechanism in a state where the first case and the second case are placed in a non-overlapping state, so that safety can be significantly improved.

That is, since the first safety means places the first case and second case are placed in the overlapping state in an overlapping state, the puncturing button cannot be pressed in this overlapping state. In this overlapping state, even if the puncturing button is pressed by any cause, the second case blocks the output of puncturing, so that the output of puncturing could not be ejected from the first and second cases.

In addition, the second safety means is provided with a puncturing starting mechanism that can operate in the non-overlapping state. In this case, after the overlapping state is released, this puncturing starting mechanism is enabled, so that the puncturing button can be operated. Therefore, the possibility of puncturing erroneously is extremely reduced.

BEST MODE FOR CARRYING OUT THE INVENTION

Figure 1:
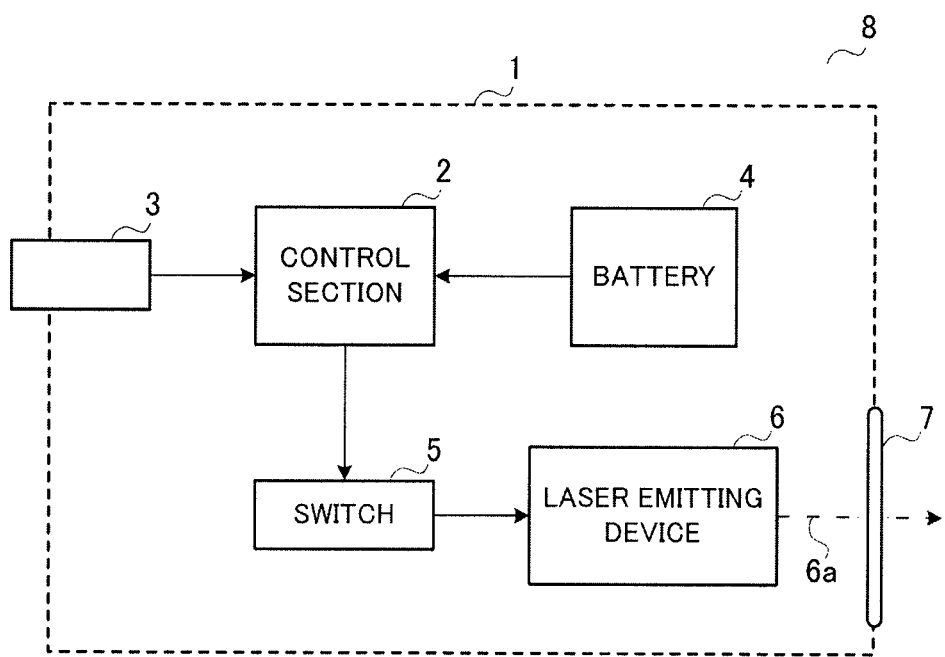
FIG. 1 is a block diagram showing a configuration of a conventional puncturing apparatus.

Now, embodiments of the present invention will be explained with reference to the accompanying drawings. Here, in description of each embodiment, directions such as the vertical direction is defined (the vertical direction of FIG. 2 means the vertical direction of the blood test apparatus in use), based on the blood test apparatus in use.

(Embodiment 1)

FIG. 2 is an external perspective view of a puncturing apparatus according to embodiment 1 of the present invention. The present embodiment is an example applied to a puncturing apparatus having a laser emitting device that punctures skin with laser light.

In FIG. 2, puncturing apparatus 111 has a configuration including: housing 112 composed of first case 112a, second case 112b and hinge part 112c; puncturing button 113 provided on the surface of first case 112a; pedestal 114as an puncturing opening that projects from first case 112a; and laser emitting device 115 (see FIG. 3) housed in first case 112a.

Figures 2A, 2B:
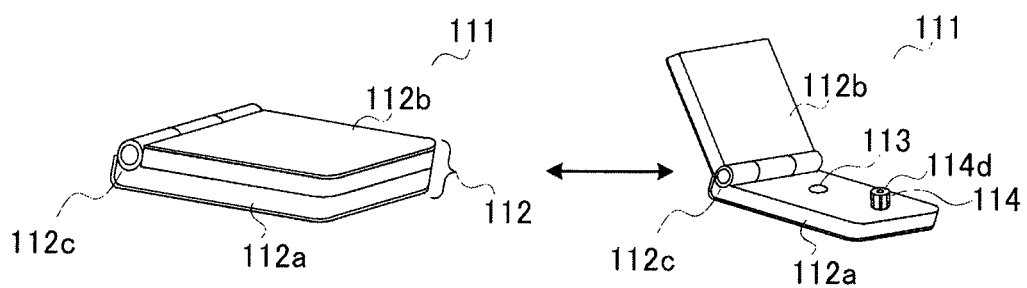
FIG. 2 is an external perspective view of a puncturing apparatus according to embodiment 1 of the present invention.

FIG. 2A shows a state where first case 112a and second case 112b are placed in the overlapping state via hinge part 112c. FIG. 2B shows a state where second case 112b is opened from first case 112a via hinge part 112c, so that first case 112a and second case 112b are placed in the non-overlapping state.

As shown in FIG. 2B, when second case 112b is opened and the non-overlapping state is made, puncturing button 113 and pedestal 114 project from the surface of first case 112a.

When pedestal is pressed in this state, a puncturing starting mechanism configured by switch 114b (see FIG. 3) is enabled. In addition, laser emitting device 115 (see FIG. 3) is housed in first case 112, and laser light 115a emitted from laser emitting device 115 penetrates pedestal 114 and punctures skin.

Puncturing button 113 is pressed while skin 9 (not shown in the figure throughout the specification, but described later in embodiment 10) of, for example, the finger of the patient touches tip 114d of pedestal 114. Then, laser light 115a is emitted and a small amount of blood 10 not shown in the figure through the specification, but described later in embodiment 10) exudes from skin 9.

In the overlapping state as shown in FIG. 2A, puncturing apparatus 111 covers puncturing button 113 with second case 112b, therefore this state can avoids the risk of pressing puncturing button 113 erroneously. Moreover, since pedestal 114 irradiated with laser light 115a (see FIG. 3 and FIG. 4) is also covered with second case 112b, laser light 115a is not emitted outside, so that safety is assured.

Furthermore, in the non-overlapping state as shown in FIG. 2B, puncturing button 113 is not enabled until switch 114b (see FIG. 4) is operated by pressing pedestal 114.

As described above, since puncturing apparatus 111 according to the present embodiment has double safety means, laser light 115a is not emitted erroneously, so that safe puncturing apparatus 11 can be provided.

In addition, since pedestal 114 projects from the surface of first case 112a, an appropriate focal distance of laser light 115a can be obtained and also the puncturing position can be clearly indicated to the user. Moreover, the overlapping state resulting from covering first case 112a with second case 112b makes the apparatus compact, which is convenient for portable use.

Figure 3:
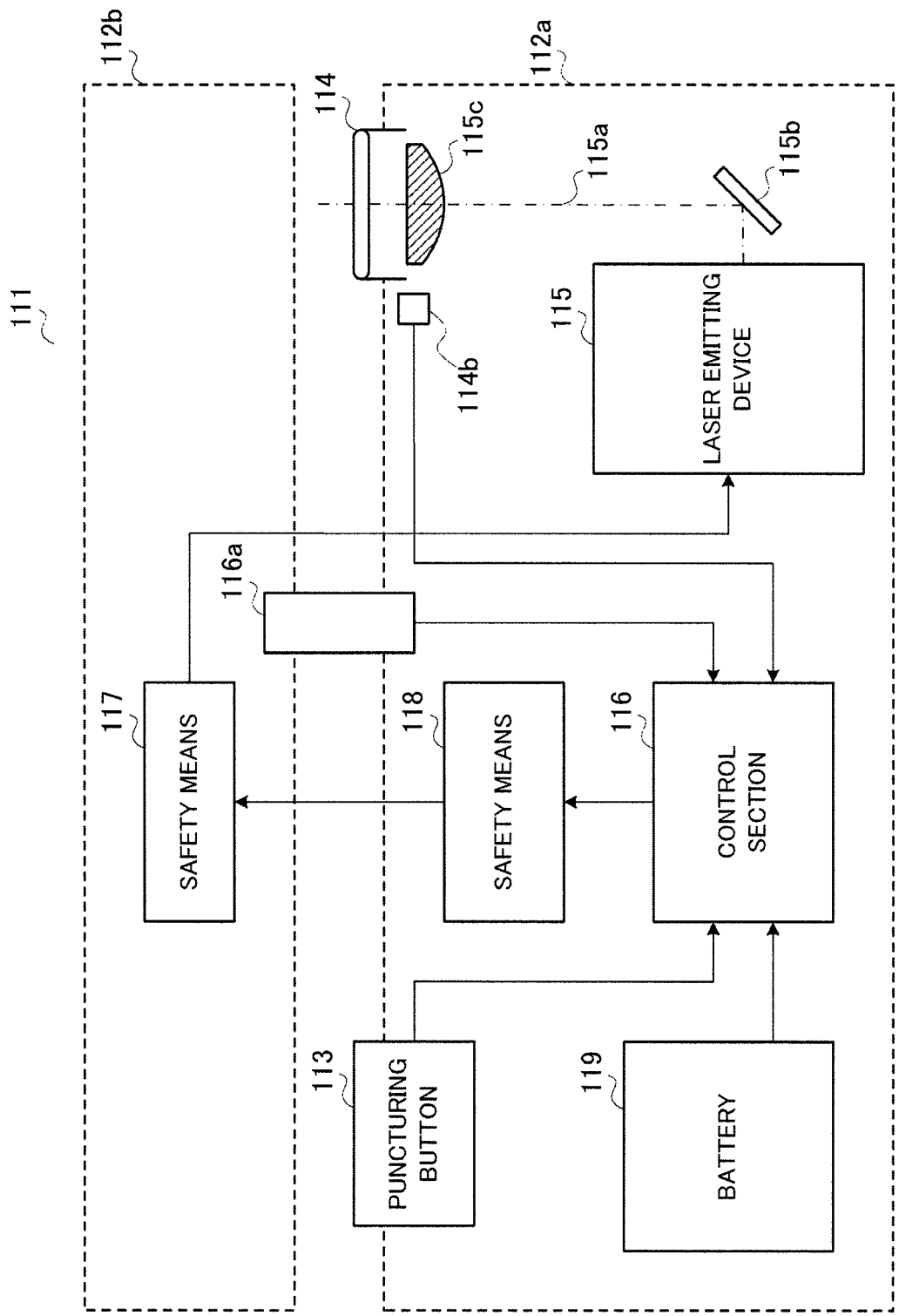
FIG. 3 is a block diagram showing a configuration of the puncturing apparatus according to embodiment 1.

FIG. 3 is a block diagram showing a configuration of puncturing apparatus 111. The same components as in FIG. 2 will be assigned the same reference numerals.

In FIG. 3, first case 112a of puncturing apparatus 111 includes control section 116 connected to puncturing button 113, battery 119 that supplies electric power to control section 116, laser emitting device (an example of puncturing means) connected to control section 116 through first safety means 117 and second safety means 118, pedestal 114 that is provided toward second case 112b side, and switch 114b that detects press the press of pedestal 114 and that is connected to control section 116.

Second case 112b includes therein first safety means 117. That is, when second case 112b is in the overlapping state, laser light 115a is prevented from emitting outside erroneously to ensure safety.

Switch 114b detects the condition of second safety means 118 and is connected to control section 116. It is not until pedestal 114 is pressed after second case 112b and first case 112a are in the non-overlapping state from the overlapping state that switch 114b is enabled to operate, so that puncturing button 113 can be pressed.

First safety means 117 detects the opening and closing of second case 112b by switch 116a and outputs the detection result to control section 116. In addition, based on the detection result from the switch 116a, when second case 112b is closed in the overlapping state, the power supply from battery 119 is cut off, so that safety is ensured and the life time of battery is extended.

Figure 4:
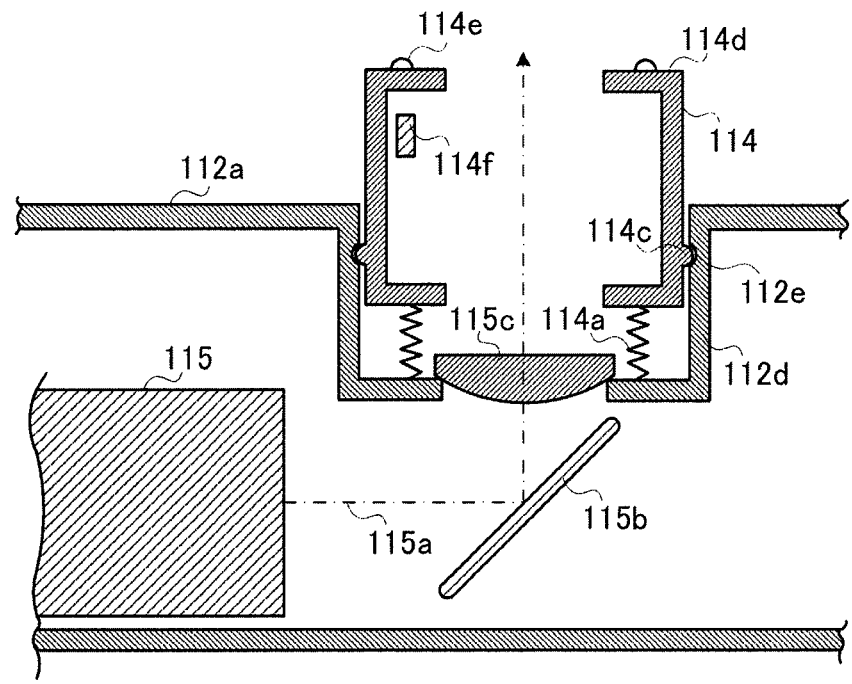
FIG. 4 is a cross sectional view showing a pedestal as an puncturing opening and its nearby primary parts, in the puncturing apparatus according to embodiment 1.

FIG. 4 is a cross sectional view showing a pedestal 114 as an puncturing opening and its nearby primary parts.

In FIG. 4, concave part 112d is formed downward from the upper surface of first case 112a, and pedestal 114 is slidably mounted in this concave part 112d. Then, pedestal 114 is biased upward by spring 114a. Switch 114b connected to control section 116 is mounted on the bottom surface of concave part 112d and detects that pedestal 114 comes down and abuts on the bottom surface. This switch 114b operates as a detecting means that enables a puncturing starting mechanism.

Positioning convex part 114c is formed on the side surface of pedestal 114 and fits in positioning concave part 112e to position pedestal 114. This positioning allows to set the distance between lens 115c and skin 9 such that laser light 115a emitted from laser emitting device 115 exactly focuses on the puncturing position in the vicinity of the surface of skin 9. Laser light 115a changes its travelling direction by 90 degrees by reflecting mirror 115b, passes through lens 115c and punctures skin 9.

Positioning convex part 114c and positioning concave part 112e are formed by conductive members. A signal from skin detecting sensor 114e mounted at tip 114d of pedestal 114 is transmitted to positioning convex part 114c through pedestal 114 and is guided to control section 116 through positioning concave part 112e in contact with positioning convex part 114c. Here, positioning convex part 114c has elasticity, so that pedestal 114 easily slides. Light receiving sensor 114f is provided inside pedestal 114, and the output of receiving sensor 114f is guided to control section 116 through positioning convex part 114c and positioning concave part 112e.

By the configuration described above, it does not enable to press puncturing button 113 until second case 112b opens and then switch 114b detects that pedestal 114 is pressed, so that the safety measure against an operation mistake is improved.

In addition, puncturing button 113 cannot be pressed until skin detecting sensor 114e detects skin 9, so that the safety measure against erroneous operation can be further improved. Moreover, light receiving sensor 114f detects light from the outside of pedestal 114. Puncturing button 113 cannot be pressed until it is detected that the output of light receiving sensor 114f is extremely decreased within a predetermined time period (i.e. the opening of pedestal 114 is closed because skin 9 touches pedestal 114, so that the external light is blocked), and therefore the safety measure against erroneous operation is improved.

Skin detecting sensor 114, light receiving sensor 114f and the fitting of positioning convex part 114c and positioning concave part 112e are detecting means that enable the puncturing starting mechanism of second safety means 118. Here, those may be individually used, or two or all may be used among the above-described three detecting means.

Figure 5:
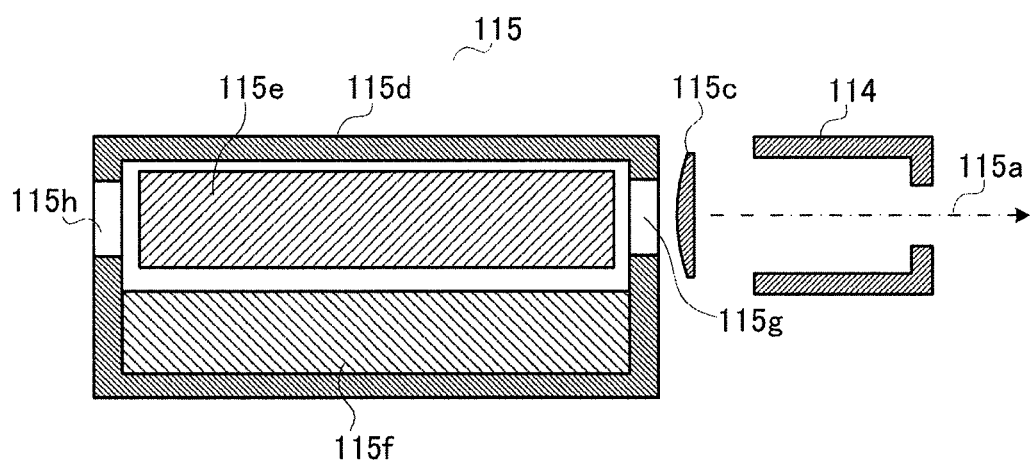
FIG. 5 is a cross sectional view showing a laser emitting device and its neighborhood of the puncturing apparatus according to embodiment 1.

FIG. 5 is a cross sectional view of laser emitting device 115 and its neighborhood.

In FIG. 5, laser emitting device 115 has oscillating tube 115d, and cylindrical pedestal 114 is placed on the down stream of oscillating tube 115d (the right side in FIG. 5). Alternatively, cylindrical pedestal 114 may be located in the direction orthogonal to oscillating tube 115d as shown in new FIG. 3. In this case, a reflecting mirror is required between pedestal 114 and oscillating tube 115d. Er:YAG (yttrium, aluminum, garnet) laser crystal 115e and flash light source 115f are housed in oscillating tube 115d.

Partially transmitting mirror 115g having a transmissivity of 3% to 15% is mounted on one end of oscillating tube 115d, meanwhile approximately total reflecting mirror 115h having a reflectivity equal to or more than 99.5% is mounted at the other end of oscillating tube 115d. Condenser lens 115c is mounted downstream of partially transmitting mirror 115g, and laser light 115a is set to focus on a position under skin 9 of the patient.

The operation of above-mentioned laser emitting device 115 will be described.

The user presses puncturing button 113 (see FIG. 3). Then, flash light source 115f emits light, and the light emitted from flash light source 115f enters Er:YAG laser crystal 115e. The light is then reflected back and forth between total reflecting mirror 115h, YAG laser crystal 115e and partially transmitting mirror 115g, resonates, and is amplified. Part of this amplified light passes through partially transmitting mirror 115g by induced emission. This laser light 115a passing through partially transmitting mirror 115g is focused on the vicinity of the surface of skin 9 by condenser lens 115c and punctures skin 9. Blood 10 exudes from the punctured skin 9. Here, light is focused such that the puncturing depth is 0.6 mm to 1.5 mm from the surface of skin 9. With the present embodiment, the puncturing depth is 1 mm.

Since the present embodiment adopts laser emitting device 115 that punctures skin 9 of the patient with light, it is not necessary to replace a puncture needle unlike a puncturing apparatus using a puncture needle, so that preparation before puncturing can be simplified. In addition, skin 9 and laser emitting device 115 do not touch each other, so that sanitary is ensured. Further, laser emitting device 115 has no moving components, so that there is little malfunction.

As described above, puncturing apparatus 111 (see FIG. 3) has: housing 112 composed of first case 112a, second case 112b and hinge part 112c; puncturing button 113 provided on the surface of first case 112a; pedestal 114 as an puncturing opening that projects from the surface of first case 112a; and laser emitting device 115 housed in first case 112a.

First safety means 117 can prohibit laser light 115a from emitting outside by erroneous operation to ensure safety when first case 112a and second case 112b are in the overlapping state. That is, the user can not operate unless opening second case 112b by covering first case 112a with second case 112b, so that the safety measure against erroneous operation can be provided.

Switch 114b detects the condition of second safety means 118 and is connected to control section 116. When pedestal 114 is pressed after the relationship between second case 112b and first 112a changes from the overlapping state to the non-overlapping state, switch 114b detects press the press of pedestal 114. This allows puncturing button 113 to be pressed.

As described above, the apparatus has second safety means 118 in addition to first safety means 117, so that safety can be significantly improved. That is, in conventional puncturing apparatuses, the safety switch can be touched on the surface of the housing and thereby it is possible to touch the safety switch erroneously during the movement and release the safety switch. In addition, since the puncturing button is exposed from the housing, it is possible to be pressed erroneously as a result of an impact when the apparatus falls. The present embodiment can prevent all above-described possibilities, so that safety can be further improved. Moreover, the overlapping state of first case 112a and second case 112b makes the housing compact as a whole, which is convenient for portable use.

(Embodiment 2)

In embodiment 2, another example of laser emitting device used for puncturing apparatus 111.

Figure 6:
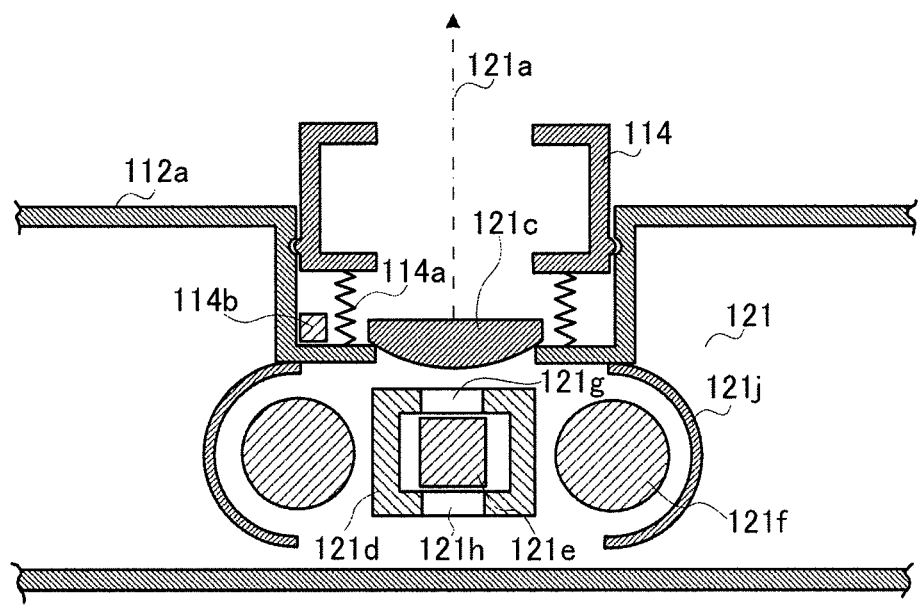
FIG. 6 is a cross sectional view showing a laser emitting device and its neighborhood, in a puncturing apparatus according to embodiment 2.
Figure 7:
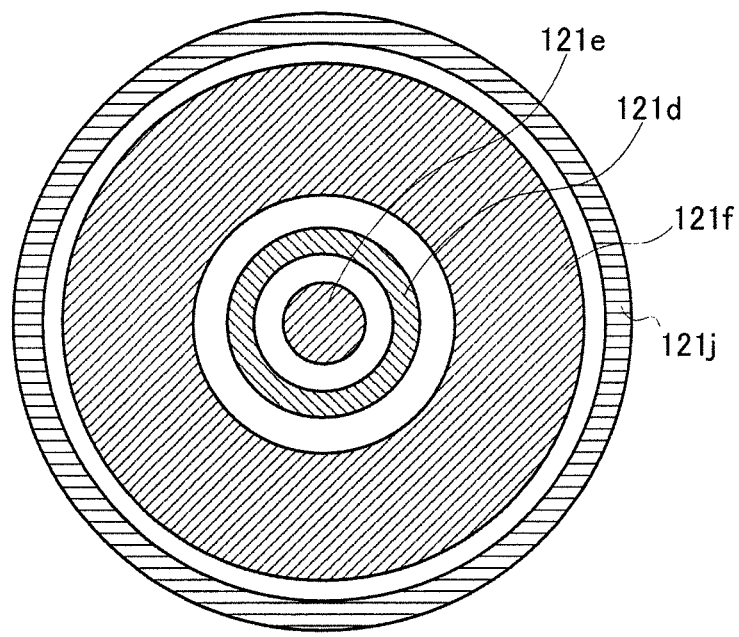
FIG. 7 is a cross sectional and plane view showing the laser emitting device of FIG. 6.

FIG. 6 is a cross sectional side view showing a laser emitting device and its nearby primary parts, and FIG. 7 is a cross sectional and plane view showing the laser emitting device of FIG. 6. The same components as in FIG. 2 in the above-described embodiment 1 will be assigned the same reference numerals and explanation for repeated parts will be eliminated. Here, components having the same alphabetical subscripts have the same functions as those of laser emitting device 115 described in the above-described embodiment 1. Hereinafter, each embodiment follows the same manner as described above.

Although flash light source 115f is arranged in parallel with laser crystal 115e in embodiment 1, flash light source 121f is provided on the outer circumference of laser crystal 121e in laser emitting device 121 according to embodiment 2. This difference will be mainly described.

As shown in FIG. 6 and FIG. 7, flash light source 121f encloses laser crystal 121e in laser emitting device 121 entirely. Partially transmitting mirror 121g is mounted in condenser lens 121c side of oscillating tube 121d, and total reflecting mirror 121h is mounted in the opposite side of partially transmitting mirror 121g.

Since flash light source 121f encloses laser crystal 121e entirely, the dimension of laser light 121a in the emitting direction can be extremely reduced. Therefore, laser emitting device 121 can be made thinner and laser emitting device 121 is suitable for portable use.

In addition, since flash light source 121f encloses laser crystal 121e, the efficiency of flash light source 121f can be improved more than laser emitting device 115 of embodiment 1 described above.

Moreover, since reflecting mirror 121j is arranged on the outside of flash light source 121f, the light from flash light source 121f can be supplied to laser crystal 121e efficiently.

(Embodiment 3)

Figures 8A, 8B:
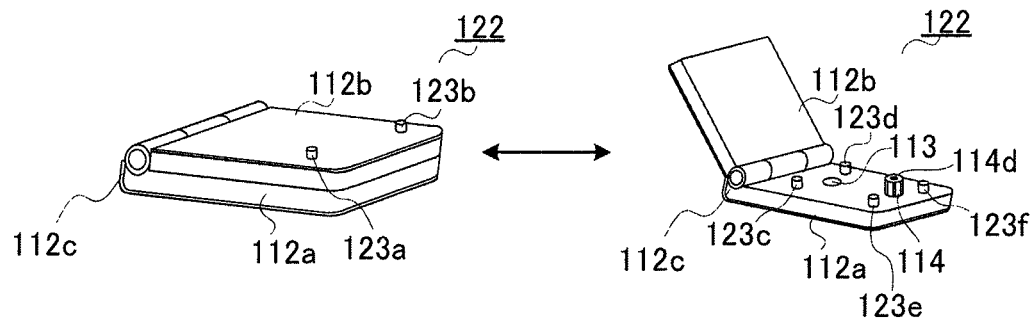
FIG. 8 is an external perspective view showing a puncturing apparatus according to embodiment 3 of the present invention.

FIG. 8A and FIG. 8B are perspective views showing a puncturing apparatus according to embodiment 3 of the present invention. FIG. 8A shows a state where first case 112a and second case 112b are placed in the overlapping state via hinge part 112c. FIG. 8B shows a state where second case 112b is opened from first case 112a via hinge part 112c, so that second case 112b and first case 112a are in placed in the non-overlapping state. The same components as in FIG. 2 will be assigned the same reference numerals and explanation for repeated parts will be eliminated.

In FIG. 8A and FIG. 8B, puncturing apparatus 122 has a configuration including: housing 112 composed of first case 112a, second case 112b and hinge part 112c; puncturing button 113 provided on the surface of second case 112b; pedestal 114 as an puncturing opening part projecting from the surface of first case 112a; safety releasing buttons 123a and 123b mounted on the upper side of second case 112b; and safety releasing buttons 123c, 123d, 123e and 123f mounted on the upper side of first case 112a. In addition, laser emitting device 115 (see FIG. 3) is housed in first case 112a, and laser light 115a emitted from laser emitting device 115 penetrates pedestal 114 as the puncturing opening part and punctures skin.

Safety releasing buttons 123a to 123f are connected to control section 116 (see FIG. 3), and control section 116 detects press the press of buttons 123a to 123f.

Safety releasing buttons 123a and 123b constitute first safety means 117A (not shown) used in the overlapping state, and safety releasing buttons 123c to 123f constitute second safety means 118A (not shown) used in the non-overlapping state. First safety means 117A according to the present embodiment has another safety means composed of safety buttons 123a and 123b in addition to first safety means 117 of FIG. 3. Moreover, second safety means 118A according to the present embodiment has another safety means composed of safety releasing buttons 123c to 123f in addition to safety means 118 of FIG. 2.

Now, the operation of puncturing apparatus 122 having the above-described configuration will be described. Since the puncturing operation is the same as in embodiment 1, the explanation will not repeated, and the operation of first safety means 117A and second safety means 118A will be described.

Two safety releasing buttons 123a and 123b are mounted on the upper side of second case 112b, which are first safety means 117A used in the overlapping state. These safety releasing buttons 123a and 123b are pressed within a predetermined time period and in a predetermined order, so that puncturing operation can be started.

Meanwhile, four safety releasing buttons 123c to 123f are mounted on the upper side of first case 123a, which are safety means 118A used in the non-overlapping state. These safety releasing buttons 123c to 123f are pressed within a predetermined time period and in a predetermined order, so that puncturing operation can be started.

As described above, puncturing apparatus 122 has first safety means 117A and second safety means 118A, so that security can be ensured and safety can be further improved as with embodiment 1.

Here, the method of releasing these safety means will be described in the present embodiment. Although embodiment 1 adopts the method of releasing the safety means using a detecting means such as a skin detecting sensor and a photodetector, the present embodiment adapts safety releasing buttons instead of the above-described detecting means unlike embodiment 1.

Although the present embodiment uses a safety releasing means composed of safety releasing buttons 123a and 123b in addition to first safety means 117 of FIG. 3 according to embodiment 1 described above, and also uses a releasing means composed of safety releasing buttons 123c to 123f in addition to safety means 118 of FIG. 3 according to embodiment 1, either the releasing means composed of safety releasing buttons 123a and 123b or the releasing means composed of safety releasing buttons 123c to 123f may be independently used.

Here, although the present embodiment has both first safety means 117a used in the overlapping state and second safety means 118A used in the non-overlapping state, another configuration having either safety means may be applicable.

In addition, the number, the mounting position and the type of safety releasing buttons 123a to 123f are not limited. Moreover, as described above, the operational sequence of 123a to 123f can be arbitrarily set.

(Embodiment 4)

Figures 9A, 9B:
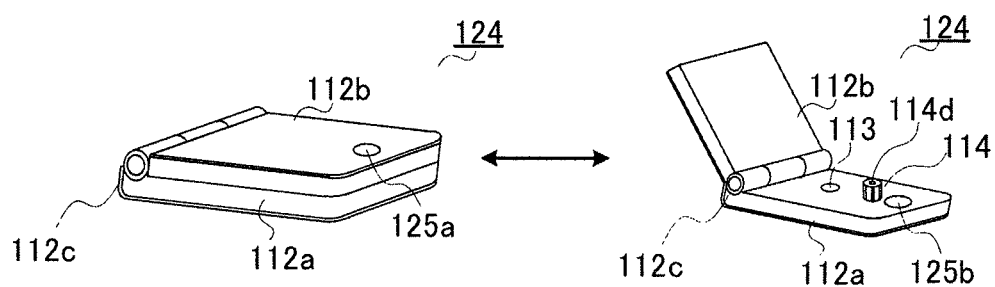
FIG. 9 is an external perspective view showing a puncturing apparatus according to embodiment 4 of the present invention.

FIGS. 9A and FIG. 9B are perspective views showing a puncturing apparatus according to embodiment 1 of the present invention. FIG. 9A shows a state where first case 112a and second case 112b are placed in the overlapping state via hinge part 112c. FIG. 9B shows a state where second case 112b is opened from first case 112a via hinge part 112c, so that first case and second case are placed in the non-overlapping state. The same components as in FIG. 2 of embodiment 1 described above will be assigned the same reference numerals and explanation for repeated parts will be eliminated.

In FIGS. 9A and 9B, puncturing apparatus 124 has a configuration including: a housing composed of first case 112a, second case 112b and hinge part 112c; puncturing button 113 provided on the surface of second case 112b; pedestal 114 as an puncturing opening that projects from the surface of first case 112a; fingerprint identifying section 125a provided on the upper side of second case 112b; and fingerprint identifying section 125b provided on the upper side of first case 112a.

Fingerprint identifying sections 125a and 125b are connected to control section 116 (see FIG. 3), and control section 116 identifies the fingerprint detected by fingerprint identifying sections 125a and 125b.

Fingerprint identifying section 125a constitutes first safety means 117b (not shown) that is used in the overlapping state, and fingerprint identifying section 125b constitutes second safety means 118B (not shown) that is used in the non-overlapping state. First safety means 117B of the present embodiment further includes a safety means configured by fingerprint identifying section 125a in addition to first safety means 117 of FIG. 3 according to embodiment 1 described above. In addition, second safety means 118B of the present embodiment further includes a safety means configured by fingerprint identifying section 125b in addition to second safety means 118 of FIG. 3 according to embodiment 1 described above.

Fingerprint identifying sections 125a and 125b identify the detected fingerprint and output the identification result to control section 116 (see FIG. 3).

Control section 116 judges the qualification of the user, based on the criterion that the fingerprint identified by fingerprint identifying sections 125a and 125b corresponds to the patient's fingerprint registered in advance.

As described above, puncturing apparatus 124 further includes fingerprint identifying sections 125a and 125b, so that safety is more improved in view of personal identification, in addition to the effect of embodiment 1.

Here, although the present embodiment has fingerprint identifying section 125a used in the overlapping state and fingerprint identifying section 125b used in the non-overlapping state, another configuration having either safety means may be applicable.

(Embodiment 5)

Figure 10:
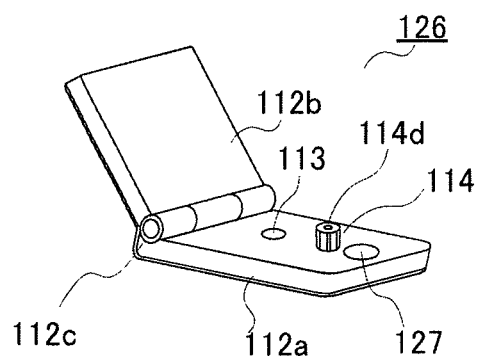
FIG. 10 is an external perspective view showing a puncturing apparatus according to embodiment 5 of the present invention.

FIG. 10 is a perspective view showing a configuration of the puncturing apparatus according to embodiment 5 in a state where second case 112b is opened from first case 112a via hinge part 112c, so that first case 112a and second case 112b are placed in the non-overlapping state. The same components as in FIG. 2 of the above-described embodiment 1 will be assigned the same reference numerals and explanation for repeated parts will be eliminated.

In FIG. 10, puncturing apparatus 126 has a configuration including: housing 112 composed of first case 112a, second case 112b and hinge part 112c; puncturing button 113 provided on the surface of second case 112b; pedestal 114as an puncturing opening that projects from the surface of first case 112a; and pointing device 127 provided on the upper surface of first case 112a.

Pointing device 127 is connected to control section 116 (see FIG. 3), and control section 116 detects the operation of pointing device 127.

Pointing device 127 constitutes second safety means 118C (not shown) used in the non-overlapping state. Second safety means 118c of the present embodiment further includes a safety means provided by operating pointing device 127 in addition to second safety means 118 of FIG. 3 in embodiment 1.

Pointing device 127 is provided on the upper side of first case 112a as safety means 118c used in the non-overlapping state. Pointing device 127 is operated in a predetermined operational sequence, so that the puncturing starting mechanism is enabled.

As described above, puncturing apparatus 126 has second safety means 118C, so that security can be ensured and safety can be further improved.

Figure 11:
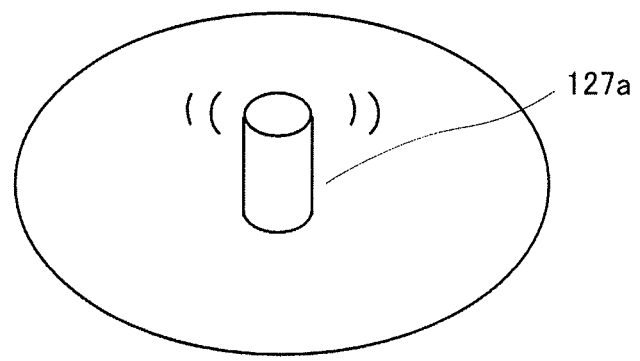
FIG. 11 is a perspective view showing an example of configuration of a pointing device of the puncturing apparatus according to embodiment 5.

FIG. 11 is a perspective view showing an exemplary configuration of pointing device 127 described above.

In FIG. 11, pointing device 127a has a knob-like shape and can release second safety means 118c by a prescribed operation to enable the puncturing starting mechanism.

Pointing device 127a having a knob-like shape is mounted on the upper side of the first case 112a, so that safety can be improved by simple operation.

Figure 12:
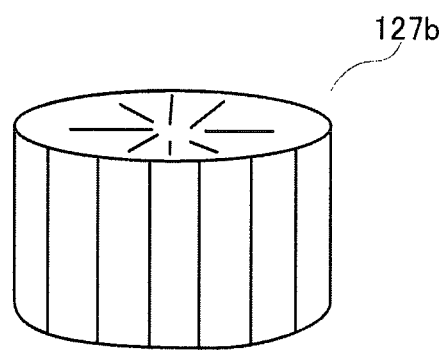
FIG. 12 is a perspective view showing an example of configuration of a pointing device of the puncturing apparatus according to embodiment 5.

FIG. 12 is a perspective view showing an exemplary configuration of pointing device 127 described above.

In FIG. 12, pointing device 127b has a pivotable volume and can release second safety means 118C by a prescribed operation to enable the puncturing starting mechanism.

Pointing device 127b configured by such volume is mounted on the upper side of first case 112a, so that the puncturing depth and the laser intensity can be adjusted by simple operation and also safety can be improved.

Figure 13:
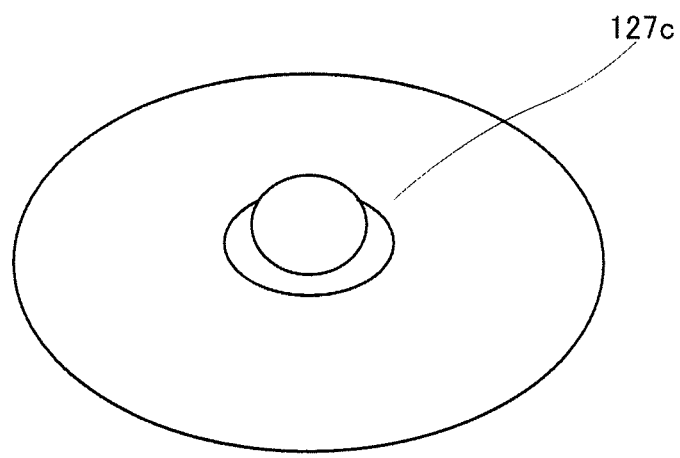
FIG. 13 is a perspective view showing an example of configuration of a pointing device of the puncturing apparatus according to embodiment 5.

FIG. 13 is a perspective view showing an exemplary configuration of pointing device 127 described above.

In FIG. 13, pointing device 127c is a trackball that can rotate in all directions and can release second safety means 118c by a prescribed operation to enable the puncturing starting mechanism.

Pointing device 127*c* configured by the trackball is mounted on the upper side of first case 112*a*, so that safety can be improved by simple operation.

Figure 14:
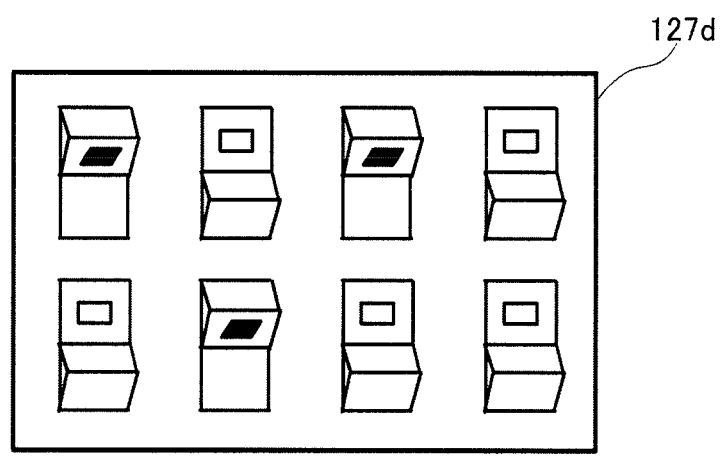
FIG. 14 is a drawing showing an example of configuration of dip switches used instead of the pointing device of the puncturing apparatus according to embodiment 5.

FIG. 14 is a drawing showing an exemplary configuration of dip switch 127*d* used instead of pointing device 127 described above.

The state of dip switch 127*d* is selected so as to correspond to a prescribed state, so that second safety means 118C can be released to enable the puncturing starting mechanism.

In addition, dip switch 127*d* is mounted on the upper surface of first case 112*a*, so that safety can be improved by simple operation.

Moreover, it is possible to provide various types of setting by using plurality of dip switches 127*d*. In addition, the number of pins of dip switch 127*d* is not limited.

(Embodiment 6)

FIG. 15 is a perspective view showing a configuration of a puncturing apparatus according to embodiment 6 of the present invention. The same components as in FIG. 1 of embodiment 1 will be assigned the same reference numerals and explanation for repeated parts will be eliminated.

In FIG. 15, puncturing apparatus 128 has a configuration including: housing 112 composed of first case 112*a*, second case 112*b* and hinge part 112*c*; inner cover 129 provided between first case 112*a* and second case 112*b*; puncturing button 113 (not shown) provided on the surface of second case 112*b*; and puncturing opening 130 projecting from the surface of first case 112*a*. In addition, second case 112*b* is provided with display section 131 (see FIG. 16). Laser emitting device 115 (see FIG. 3) is housed in first case 112*a*, and laser light 115*a* emitted from laser emitting device 115 penetrates puncturing opening 130 and punctures skin.

Puncturing apparatus 128 includes inner cover 129 between first case 112*a* and second case 112*b*.

Figures 15A, 15B, 15C:
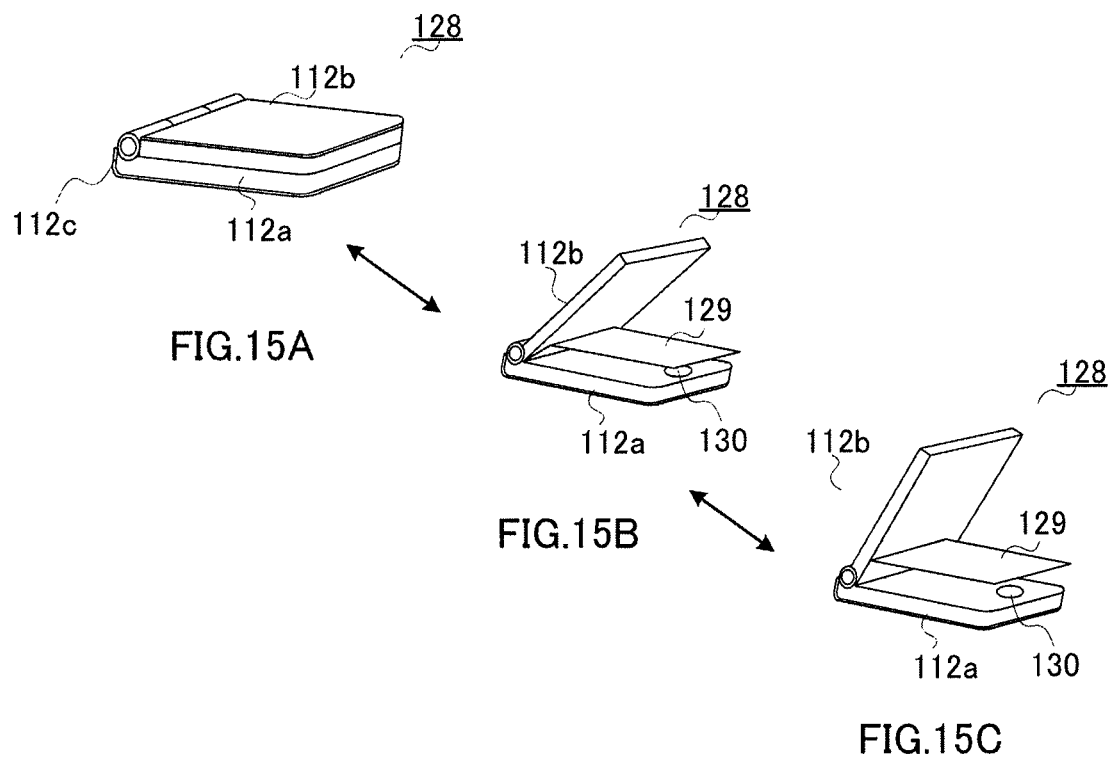
FIG. 15 is a perspective view showing a configuration of a puncturing apparatus according to embodiment 6 of the present invention.

FIG. 15A shows a state where first case 112*a* and second case 112*b* are closed via hinge part 112*c*; FIG. 15B shows a state where second case 112*b* is open at the first level, from first case 112*a*; and FIG. 15C shows a state where second case 112*b* is open at the second level, from first case 112*a* up to a puncturing capable position via hinge part 112*c*.

In the opening state at the first level as shown in FIG. 15B, inner cover 129 is located between first case 112*a* provided with puncturing opening section 130 and second case 112*b*. In such state, then puncturing is performed. At this time, inner cover 129 serves as first safety means 117C (not shown) so as to prevent laser light 115*a* from leaking outside.

In the opening state at the second level as shown in FIG. 15C, the display of display section 131 (see FIG. 16) provided in second case 112*b* can be viewed. Here, this display section 131 can be used as a display section of blood test apparatus 141 of embodiment 10 described later. In this case, large display section 131 can fill the entire case 112*b*, so that it is possible to provide a screen, which is easily viewable to the patient with poor eyesight.

(Embodiment 7)

FIG. 16 is a perspective view showing a configuration of a puncturing apparatus according to embodiment 7 of the present invention. Here, the same components as in FIG. 1 of embodiment 1 will be assigned the same reference numerals and explanation for repeated parts will be eliminated.

In FIG. 16, puncturing apparatus 132 has a configuration including: housing 112 composed of first case 112*a*, second case 112*b* and hinge part 112*c*; puncturing button 113 (not shown) provided on the surface of second case 112*b*; and puncturing opening 130 provided on the surface of first case 112*a*. In addition, second case 112*b* is provided with display section 131. Laser emitting device 115 (see FIG. 3) is provided in first case 112*a*, and laser light 115*a* emitted from laser emitting device 115 penetrates puncturing opening 130 and punctures skin.

Figures 16A, 16B, 16C:
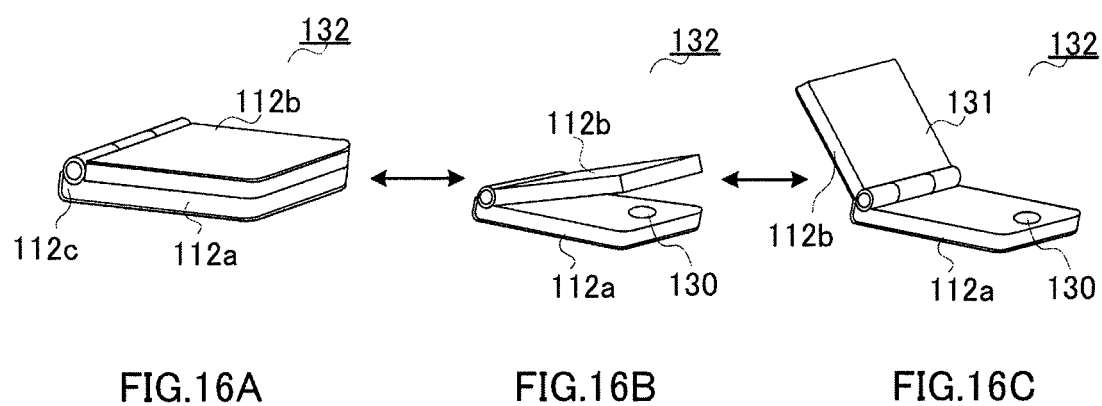
FIG. 16 is an external perspective view of a puncturing apparatus according to embodiment 7 of the present invention.

FIG. 16A shows a state where first case 112*a* and second case 112*b* are closed via hinge part 112*c*; FIG. 16B shows a state second case 112*b* is open at the first level, from first case 112*aat*; and FIG. 16C shows a state where second case 112*b* is open at the second level, from first case 112*a* up to a puncturing capable position via hinge part 112*c*.

Puncturing apparatus 132 performs puncturing in the state where puncturing apparatus 132 is open at the first level as shown in FIG. 16B. That is, puncturing apparatus 132 can perform puncturing in the position where puncturing opening 130 is covered with second case 112*b* as shown in FIG. 16B. In addition, puncturing apparatus 132 is prevented from puncturing in the state where the puncturing apparatus 132 is open at the second level as shown in FIG. 16C. For example a mechanical switch provided in hinge part 112*c* detects puncturing apparatus 132 in the state shown in FIG. 16B is.

In the present embodiment, second case 112*b* itself serves as first safety means 117D (not shown) so as to prevent laser light 115*a* from leaking outside.

FIG. 16C shows the overlapping state at the second level where the cases are open at a large angle. In this sate, the display of measurement data and so forth can be viewed by display section 131 provided in second case 112*b*. Here, this display section 131 can be effectively used as a display section of blood test apparatus 141 of embodiment 10 described later.

(Embodiment 8)

Figure 17:
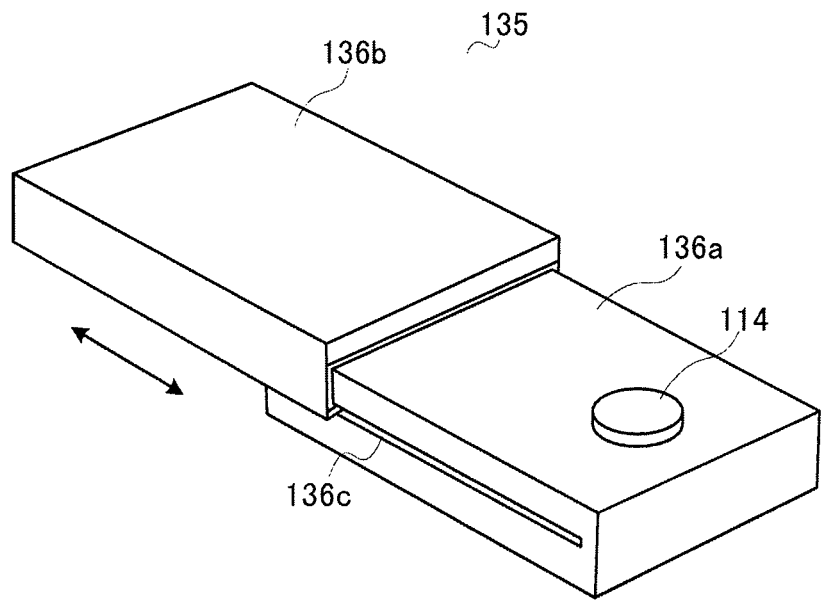
FIG. 17 is an external perspective view of the puncturing apparatus according to embodiment 8 of the present invention.

FIG. 17 is a perspective view showing a configuration of a puncturing apparatus according to embodiment 8 of the present invention. Here, the same components as in FIG. 1 of embodiment 1 will be assigned the same reference numerals and explanation for repeated parts will be eliminated.

In FIG. 17, puncturing apparatus 135 has a configuration including: first case 136*a*; second case 136*b* that slides on the surface of first case 136*a* through guide 136*c* provided on the side surface of first case 136*a*; and pedestal 114 as an puncturing opening, which projects from the surface of second case 136*b*. Laser emitting device 115 (see FIG. 3) is housed in first case 136*a*, and laser light 115*a* emitted from laser emitting device 115 penetrates an opening of pedestal 114 (not shown)and punctures skin.

In the present embodiment, second case 136*b* slides through guide 136*c* provided on the side surface of first case 136*a*. By this means, the overlapping state and the non-overlapping state can be made. First safety means 117E (not shown) operates to prevent laser light 115 from leaking from second case 136*b* to the outside.

(Embodiment 9)

Figure 18:
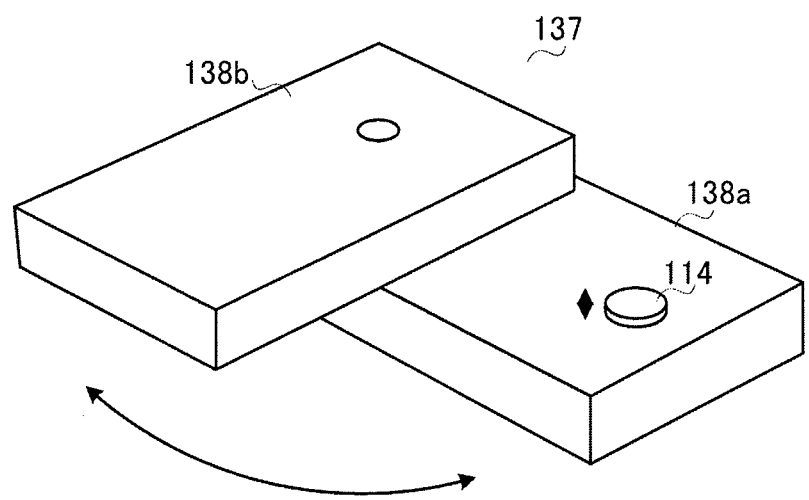
FIG. 18 is an external perspective view of the puncturing apparatus according to embodiment 9 of the present invention.

FIG. 18 is a perspective view showing a configuration of a puncturing apparatus according to embodiment 9 of the present invention. Here, the same components as in FIG. 1 of embodiment 1 described above will be assigned the same reference numerals and explanation for repeated parts will be eliminated.

In FIG. 18, puncturing apparatus 137 has a configuration including: first case 138*a*; second case 138*b* that pivotally turns or rotates in the horizontal direction around the axis in one end of first case 138*a*; and pedestal 114 as an puncturing opening, which projects from the surface of second case 138*b*. Laser emitting device 115 (see FIG. 3) is housed in first case 138*a*, and laser light 115*a* emitted from laser emitting device 115 penetrates pedestal 114 and punctures skin.

With the present embodiment, second case 138*b* pivotally turns or rotates in the horizontal direction through one end of first case 138a. By this means, the overlapping state and the non-overlapping state can be made. First safety means 117F (not shown) operates so as to prevent laser light 115 from leaking from second case 136b to the outside.

(Embodiment 10)

Figure 19:
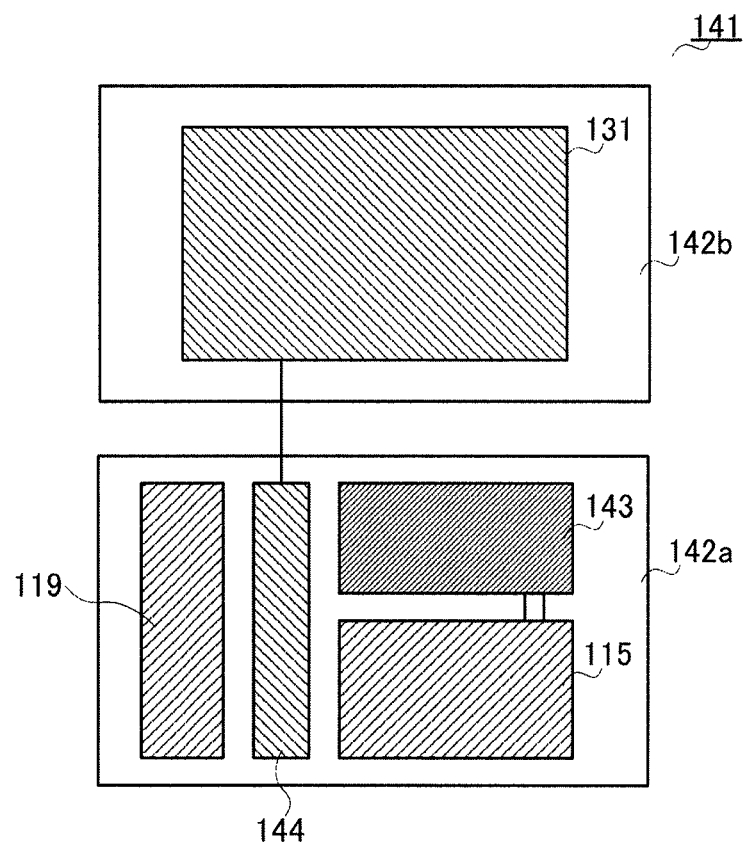
FIG. 19 is a cross sectional view showing a configuration of a blood test apparatus according to embodiment 10 of the present invention.

FIG. 19 is a cross sectional view showing a configuration of a blood test apparatus according to embodiment 10 of the present invention. The present embodiment is an example applied to a blood test apparatus having a puncturing apparatus that punctures skin through a blood sensor.

The blood test apparatus according to the present embodiment employs puncturing apparatuses 111, 122, 124, 126, 128, 132, 135 and 137 for respective embodiments 1 to 9, and first safety means 117 and second safety means 118 used for those puncturing apparatuses.

In FIG. 19, blood test apparatus 141 has first case 142a and second case 142b. For example, first case 142a corresponds to first case 112a of FIG. 2 and second case 142b corresponds to second case 112b of FIG. 2 in the above-described embodiment 1.

Blood test apparatus 141 of the present embodiment may be applied to puncturing apparatuses 122, 124, 126, 128, 132, 135 and 137 in embodiments 2 to 9, and in this case, corresponding first and second cases are used.

Laser emitting device 115, negative pressure means 143, electrical circuit section 144 that controls laser emitting device 115 and negative pressure means 143, and battery 119 that supplies power to each section are housed in first case 142a. In addition, display section 131 connected to electrical circuit section 144 is housed in second case 142b. Then, those first case 142 and second case 142 are movable so as to create the overlapping state and the non-overlapping state. The overlapping state and the non-overlapping state can be made by the method in each embodiment described above.

Figure 20:
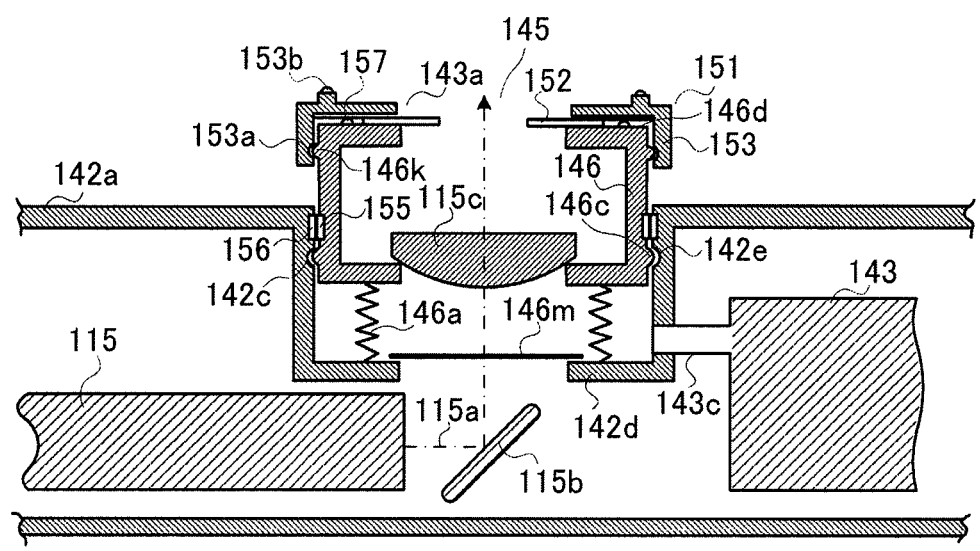
FIG. 20 is a cross sectional view of a pedestal as an puncturing opening and its nearby primary part, in the blood test apparatus according to embodiment 10.

FIG. 20 is a cross sectional view of a pedestal as an puncturing opening and its nearby primary parts. Here, the components the same as those of pedestal 114 in FIG. 4 of embodiment 1 and in FIG. 6 in embodiment 2 described above are assigned the same alphabetical subscripts, so that the explanation is simplified.

In FIG. 20, pedestal 146 forming puncturing opening 145 is slidably mounted in concave portion 142b formed downward from the upper surface of first case 142a and is biased upward by spring 146a.

Positioning convex part 146c is formed on the side surface of pedestal 146 and fits in positioning concave part 142e formed in concave part 142d to position pedestal 146. By this positioning, it is possible to accurately set laser light 115a emitted from laser emitting device 115 so as to focus on the vicinity of the surface of skin 9. Here, laser light 115a changes its traveling direction by 90 degrees by reflecting mirror 115b, passes through condenser lens 115c and punctures skin 9.

Sensor unit 151 is removably mounted at tip 146d of pedestal 146. Blood sensor 152 is removably mounted in sensor unit 151. Then, connection electrodes 171 (171a to 175a) (see FIG. 22 described later) formed on this blood sensor 152 contact connectors 157 (157a to a57f) formed at tip 146 of pedestal 146. Connectors 157 are connected to connectors 155 (155a to 155f) formed on the side surface of pedestal 146 through conducting wires. These connectors 155 are connected to connectors 156 (156a to 156f) formed in concave part 142d of case 142a through conducting wires. Then, these connectors 156 are connected to electrical circuit section 144 through conducting wires.

Positioning concave part 153a that positions pedestal 146 is formed on holder 153 constituting sensor unit 151, and positioning convex part 146k formed on the side surface of pedestal 146 fits in this positioning concave part 153a, so that positioning is achieved. In addition, negative pressure chamber 143a that applies a negative pressure to the vicinity of blood sensor 152 is formed in holder 153. Skin detecting sensor 153 is provided on a surface, in contact with skin 9, of this negative pressure chamber 143a.

Positioning convex parts 146c and 146k and positioning concave parts 142e and 153a are made of conductive members, and a signal from skin detecting sensor 153b formed in sensor unit 151 is guided to electrical circuit section 144 through those positioning concave part 153a, positioning convex part 146k, positioning convex part 146c and positioning concave part 142e in the described order. Here, positioning convex parts 146c and 146k have elasticity to easily slide pedestal 146.

Transparent member 146m is attached to the bottom of concave part 142d, and this transparent member 146m allows laser light to pass through without loss but does not allow a negative pressure to passing through. In addition, a negative pressure is created in concave part 142, pedestal 146 and negative pressure chamber 143a. This it is possible to acquire this negative pressure by supplying a negative pressure from negative pressure means 143 to concave part 142 through negative pressure path 143c.

Figure 21:
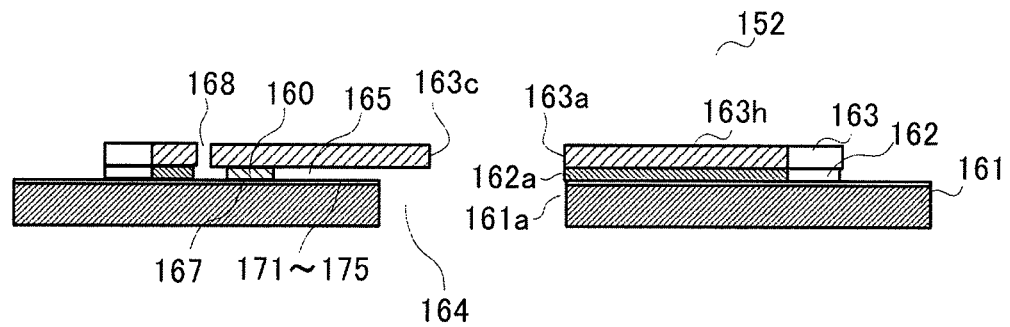
FIG. 21 is a cross sectional view of a blood sensor mounted in a sensor unit of the blood test apparatus according to embodiment 10.

FIG. 21 is a cross sectional view of blood sensor 152 mounted in sensor unit 151.

In FIG. 21, blood sensor 152 is composed of substrate 161, spacer 162 pasted on the upper surface of this substrate 161 and cover 163 pasted on the upper surface of this spacer 162, and has a plate-like shape.

Storing section 164 that stores blood 10 is formed by substrate hole 161a formed at approximately the center of substrate 161, spacer hole 162a formed at approximately the center of spacer 162 and cover hole 163a formed at approximately the center of spacer 163 that communicate with storing section 164, respectively.

This storing section 164 is open downward in order to touch skin 9 and sample blood 10 (note that it is open upward when actually used). In addition, supply path 165 that supplies blood 10 is coupled to storing section 164. On end of this supply path 165 is coupled to storing section 164 and guides blood 10 stored in storing section 164 to detecting section 167 (see FIG. 22) formed on supply path 165 by capillary action. Meanwhile, the other end of supply path 165 is coupled to air hole 168.

Here, a water-repellent material is used for the upper surface 163h of cover 163. Meanwhile, a hydrophilic material is used for inside supply path 165. Here, preferably, top surface 164a of storing section 164 is subject to hydrophilic treatment softer than that for supply path 165, or is subject to water repellent finish softer than that for the upper surface 163h of cover 163.

Reagent 167 is placed on detecting section 167. This reagent 160 can be obtained by adding and dissolving PQQ-GDH (0.1 to 5.0 U/sensor), potassium ferricyanide (10 to 200 millimole), maltitol (1 to 50 millimole) and taurine (20 to 200 millimole) in a CMC solution of 0.01 to 2.0 wt % to prepare a reagent solution, by dropping the reagent solution on detection electrodes 171 and 173 (see FIG. 22) formed on substrate 161 and drying.

Figure 22:
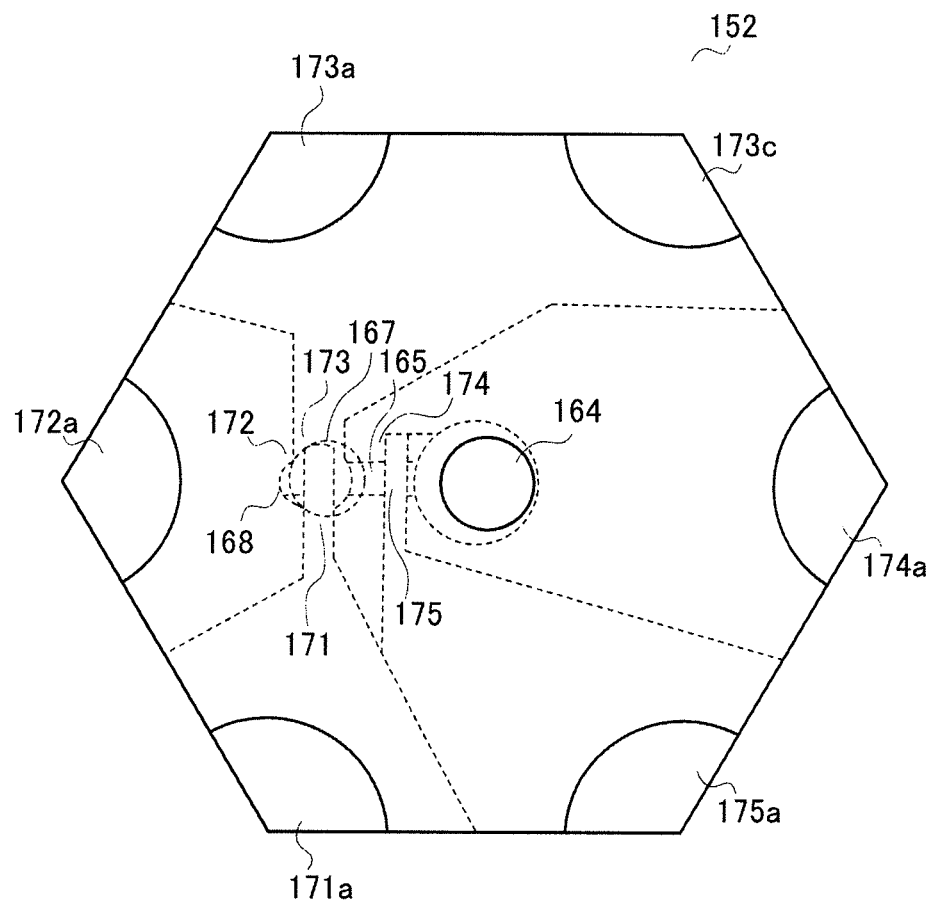
FIG. 22 is a perspective plane view of the blood senor of the blood test apparatus according to embodiment 10.

FIG. 22 is a perspective plane view of blood sensor 152 described above.

As shown in FIG. 22, the shape of blood sensor 152 is a regular hexagon, and connection electrodes 171a to 175a connected to connectors 157 (157a to 157f) provided on pedestal 146 and reference electrode 173c connected to connection electrode 173a are formed in its respective six top parts.

Storing section 164 that stores blood 10 is provided at approximately the center of blood sensor 152. Supply path 165 having one end connected to this storing section 164 is provided toward detection electrode 172. The other end of this supply path 165 is coupled to air hole 168. Storing section 164, detection electrode 174 connected to connection electrode 174a, detection electrode 175 connected to connection electrode 175a, again detection electrode 174 connected to connection electrode 174a, detection electrode 173 connected to connection electrode 173a and reference electrode 173c, detection electrode 171 connected to connection electrode 171a, again detection electrode 173 connected to connection electrode 173a and reference electrode 173c and detection electrode 172 connected to connection electrode 172a, are provided on supply path 35 in the described order. In addition, reagent 160 (see FIG. 21) is placed on detection electrodes 171 and 173.

Connection electrodes 171a to 175a and 173c are formed in respective regular-hexagonal shaped top parts of blood sensor 152.

Moreover, in FIG. 20 described above, guide section 176 (see FIG. 23) is formed for sensor unit 151, pedestal 146 and concave section 142d. It is possible to easily and securely insert, in pedestal 146, sensor unit 151 in which blood sensor is mounted by forming guide section 176 for sensor unit 151, pedestal 146 and concave section 142d. In addition, even if sensor unit 151 is inserted in pedestal 146 in a careless way, the signal from sensor unit 152 can be certainly transmitted to electrical circuit section 144.

Figure 23:
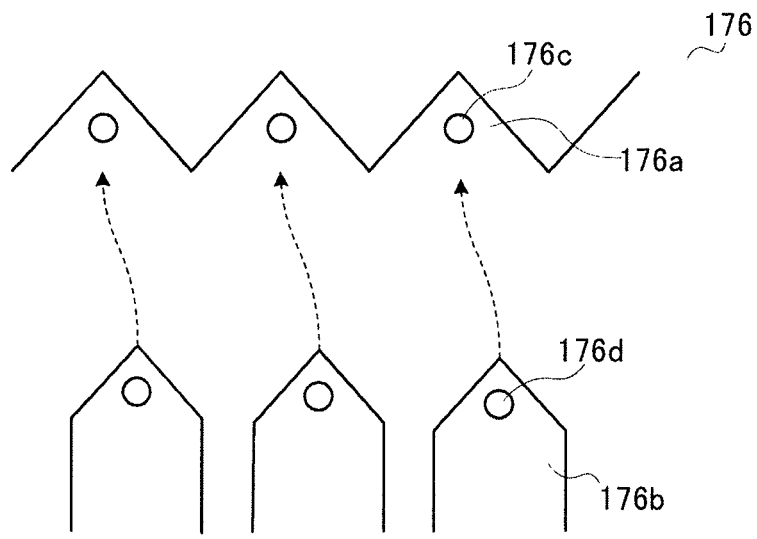
FIG. 23 is a developed plane view of a guide section of the blood test apparatus according to embodiment 10.

FIG. 23 is a developed plane view of the above-described guide section 176.

In FIG. 23, guide section 176 has concave-shaped guide 176a formed on the side surface of pedestal 146 and convex-shaped guide 176b formed inside sensor unit 151 and inside the upper side of concave part 142d.

Even if the sensor unit 151 is inserted in a careless way, the inserting direction is corrected along those guides 176a and 176b during insert of sensor unit 151. By this means, the electrodes are reliably connected to one another so that the signal of blood test apparatus 152 can be reliably guided to electrical circuit section 144.

Convex part 176c having conductivity and elasticity is formed in the innermost part of guide 176a, and concave part 176d is formed at the tip of guide 176b. Convex part 176c fits in concave part 156d to position sensor unit 151 and pedestal 146, and the signal from skin detecting sensor 153b mounted in sensor unit 151 through those convex part 176c and concave part 176d is guided to electrical circuit section 144. Here, concave part 176d corresponds to positioning concave parts 142e and 153a, and convex part 176c corresponds to positioning convex parts 146c and 146k in FIG. 20.

Figure 24:
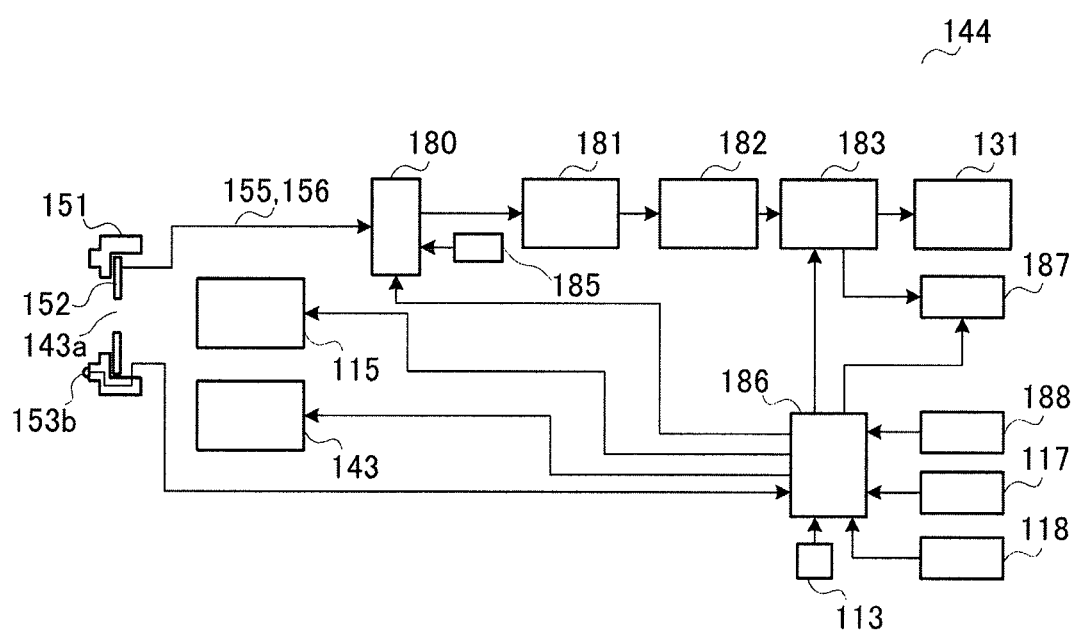
FIG. 24 is a block diagram of an electrical circuit section and its periphery, in the blood test apparatus according to embodiment 10.

FIG. 24 is a block diagram showing electrical circuit section 144 described above and its periphery.

In FIG. 24, connection electrodes 171a to 175a and reference electrode 173c are connected to switching circuit 180 through connectors 155 (155a to 155f) and connectors 156 (156a to 156f). The output of switching electrode 180 is inputted to current/voltage convertor 181. The output of current/voltage convertor 181 is inputted to computing section 183 through analog/digital convertor 182 (hereinafter referred to as "A/D convertor"). The output of computing section 183 is inputted to display section 131 made of liquid crystal, and transmitting section 187. Reference voltage source 185 is connected to switching circuit 180. Here, this reference voltage source 185 may be a ground potential.

Control section 186 is configured by, for example, a microcomputer and controls entirely the puncturing and blood-testing operations of the puncturing apparatus and blood test apparatus 141. Each detection signal of puncturing button 113 that activates laser emitting device 115, skin detecting sensor 153b, timer 188, first safety means 117 and second safety means 118 is inputted to control section 186, and control section 186 outputs each control signal to laser emitting device 115, a control terminal of switching circuit 180, computing section 183, transmitting section 187 and negative pressure means 143. Here, a negative pressure button that is pressed by the hand may be connected and used instead of skin detecting sensor 153b.

next, the operation of electrical circuit section 144 will be described.

First, control section 186 detects which of connectors 156 (156a to 156f) connects connection electrodes 171a to 175a and reference electrode 173 of blood sensor 152, respectively. Here, connectors 157 (157a to 157f) are connected to connectors 156 (156a to 156f) through connectors 155 (155a to 155f). That is, control section 186 finds connector 156 having zero electrical resistance to the adjacent connector, among connectors 156. Then, when connector 156 having zero electrical resistance is touched, control section 186 determines that that is connector 156 to be connected to reference electrode 173. Then, based on connector 156 connected to this reference electrode 173c, control section 186 sequentially detects electrical resistance of connection electrodes 174a, 175a, 171a, 172a, 173a, reference electrode 173a and connectors 156 (starting from one of connectors 156a to 156f) in the described order. As described above, control section 186 determines respective connector 156a to 156f connected to connection electrodes 171a to 175a and reference electrode 173c, and then goes into measurement of blood 10.

In measurement operation, control section 186 firstly switches switching circuit 180 and connects detection electrode 171 (see FIG. 2) that is to be a working electrode for measuring blood components to current/voltage convertor 181. In addition, control section 186 connects detection electrode 172 to be a detection electrode for detecting inflow of blood 10 to reference voltage source 185. Then, control section 186 applies a constant voltage between detection electrode 171 and detection electrode 172. In this state, when blood 10 flows in, a current flows between detection electrodes 171 and 172. This current is converted into a voltage by current/voltage convertor 181 and the voltage value is converted into a digital value by A/D convertor 182. Then, the digital value is outputted to computing section 183. Computing section 183 detects the sufficient inflow of blood 10 based on this digital value. Here, at this time, the operation of negative pressure means 143 is turned off.

Next, glucose, which is a component of blood will be measured.

In order to measure the glucose level, control section 186 firstly switches switching circuit 180 and connects detection electrode 171 to be a working electrode for measuring the glucose level to current/voltage convertor 181. In addition, detection electrode 173 to be a counter electrode for measuring the glucose level, is connected to reference voltage source 185.

Here, for example, while the glucose in blood and its oxidation-reduction enzyme react for a certain period of time, current/voltage convertor 181 and reference voltage source 185 are turned off. Then, after the certain period of time (1 to 10 seconds) passes, control section 186 applies a constant voltage (0.2 to 0.5 V) between detection electrodes 171 and 173. By this means, a current flows between detection electrodes 171 and 173. This current is converted into a voltage by current/voltage convertor, and the voltage value is converted into a digital value by A/D convertor 182 and is outputted to computing section 183. Computing section 183 converts this digital value into the glucose level and measures the glucose level.

Next, after the glucose level is measured, a Hct value is measured.

The Hct value will be measured as follows. Firstly, control section 186 switches switching circuit 180. Then, control section 186 connects detection electrode 175 to be a working electrode for measuring the Hct value to current/voltage convertor 181. In addition, control section 186 connects detection electrode 171 to be a counter electrode for measuring the Hct value is connected to reference voltage source 185.

Control section 186 then applies, from current/voltage convertor 181 and reference voltage source 185, a constant voltage (2V to 3V) between detection electrodes 175 and 171. The current flown between detection electrode 175 and detection electrode 171 is converted into a voltage by current/voltage convertor 181, and the voltage value is converted into a digital value by A/D convertor 182 and is outputted to computing section 183. Computing section 183 converts this digital value into Hct value and measures Hct value.

By using the Hct value and the glucose level resulting from the measurement and by referring to a calibration curve or calibration curve table determined in advance, control section 186 corrects the glucose level by the Hct value and displays the correction result on display section 131. In addition, transmitting section 187 transmits this correction result to an injection device that injects insulin. Although a radio wave may be used for this transmission, transmission is preferably performed by optical communication that does not interfere with medical equipment.

The injection device may be automatically set the dose of insulin, based on measurement data transmitted from transmitting section 187. By such configuration, it is not necessary to set the dose of insulin to be administered in the injection device, which eliminates the burden of setting. Moreover, since the dose of insulin can be set in the injection device without human work, setting error can be prevented.

Although an example of glucose measurement has been described, the blood test apparatus is applicable to measure blood components other than glucose such as lactate acid or cholesterol levels by changing reagent 160 of blood sensor 152.

Next, the operation of blood test apparatus 141 will be described.

Figure 25:
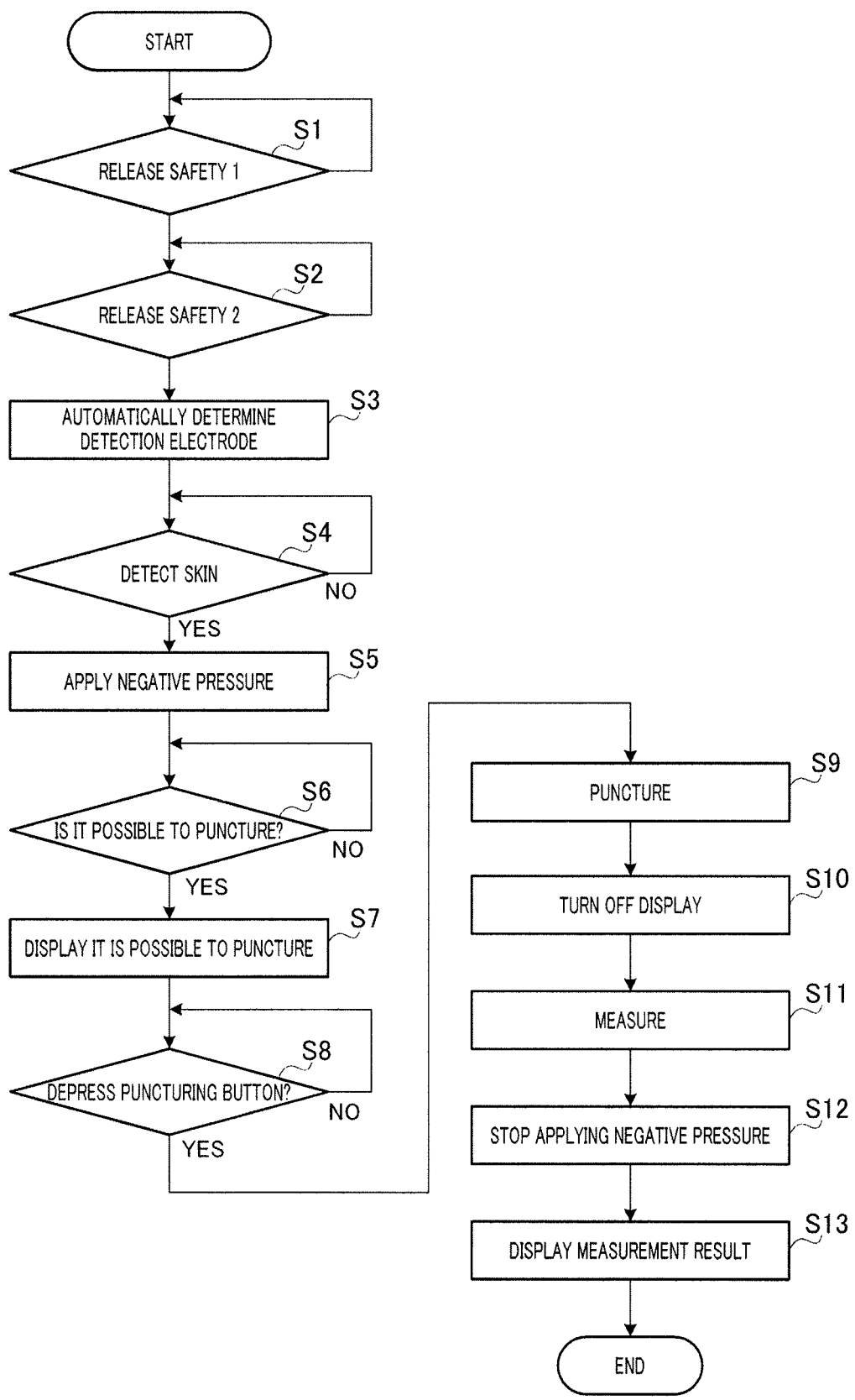
FIG. 25 is a flowchart showing operation of the blood test apparatus according to embodiment 10.

FIG. 25 is a flowchart showing the operation of blood test apparatus 141. Control section 186 is configured by a microprocessor, for example. The flow is repeatedly performed by this microprocessor at a predetermined timing.

First, in step S1, control section 186 waits to release first safety means 117. When first safety means 117 is released, the step moves step S2, and control section 186 waits to release second safety means 118 in step S2. First safety means 117 and second safety means 118 correspond to puncturing apparatuses 111, 122, 124, 126, 128, 132, 135 and 137 of embodiments 1 to 9.

When second safety means 118 is released in step S2, the step moves to step S3.

In step S3, control section 186 determines detection electrodes of blood sensor 152. That is, control section 186 firstly detects reference electrode 173c and identifies detection electrodes 171 to 175, based on this detection in reference electrode 173c.

In this case, although an example of blood sensor 152 having reference electrode 173c has been illustrated, this step S3 can be eliminated if the blood sensor does not have a reference electrode (i.e. each electrode is fixed in advance and the mounting direction is also fixed).

In step S4, control section 186 waits for contact with skin 9 from which blood is sampled. To more specific, when skin detecting sensor 153b of sensor unit 151 detects skin 9, control section 186 determines that there is contact with skin 9 from which blood is sampled. When skin 9 is detected, the step moves to step S5. Here, instead of skin detecting sensor 153b, negative pressure button (not shown) is connected to control section 186 and this negative pressure button may be pressed.

In step S5, control section 186 activates negative pressure means 143. Negative pressure means 143 applies a negative pressure to negative pressure chamber 143a (the vicinity of blood sensor 152).

In step S6, control section 186 determines whether it is possible to perform puncturing. That is, control section 186 determines that skin 9 sufficiently has swelled within storing section 164, based on change in the current of a vacuum pump constituting negative pressure chamber 143, or when timer 188 measures a predetermined time period.

In step S7, control section 186 displays that it is possible to perform puncturing on display section 131.

In step S8, control section 186 determines whether the patient presses puncturing button 113 according to this display.

When the patient presses puncturing button 113, control section 186 instructs laser emitting device 115 to emit laser light in step S9. Laser emitting device 115 emits laser light 115a and laser light 115a punctures skin 9.

In step S10, control section 186 turns off the display indicating that it is possible to perform puncturing, displayed on display section 131. After puncturing is completed, it is preferable to immediately turn off the display indicating that it is possible to perform puncturing, in order to prevent the patient from pressing puncturing button 113 again.

In step S11, control section 186 measures the blood sugar level of blood 10. In the above-described step S9, blood 10 exudes by puncturing skin 9. This blood 10 is taken into detecting section 167 (see FIG. 21) of blood sensor 152. Control section 186 switches switching circuit 180, connects detection electrode 171 to be a working electrode for measuring the glucose level to current/voltage convertor 181, and connects detection electrode 173 to be a counter electrode for measuring the glucose level to reference voltage source 185, in order to measure the glucose level. When the blood sugar level is measured, the step moves to step S12.

In step S12, control section 186 turns off the operation of negative pressure means 143. Alternatively, in step S11, negative pressure means 143 may be turned off at the time blood 10 reaches (i.e. when blood 10 reaches detection electrode 172, which is a detecting electrode). Negative pressure means 143 is preferably turned off at this timing in view of stability of the measurement operation.

In step 13, control section 186 displays the measured value of the blood sugar level on display section 131 and terminates the present flow.

Although an instance has been described in detail where blood test apparatus 141 employs puncturing apparatus 111 as shown in the above-described embodiment 1, puncturing apparatus 111 has first safety means 117 and second safety means 118 as with puncturing apparatuses 122, 124, 126, 128, 132, 135 and 137 as shown in embodiments 2 to 9 described above, so that safety-conscious blood test apparatus 141 can be achieved. In addition, first case 142a and second case 142b are placed in the overlapping state, so that an effect that makes the whole apparatus compact, which is convenient for portable use is obtained.

Although the present embodiment further includes a negative pressure means that applies a negative pressure to the vicinity of the blood sensor, the present invention is not limited to the negative pressure but swelling by pressing skin may be applicable.

(Embodiment 11)

Embodiments 11 to 19 will describe in detail the configurations of embodiments 1 to 9 described above.

FIG. 26 is a perspective view showing a configuration of a puncturing apparatus according to embodiment 11 of the present invention. Here, the same components as in FIG. 2 and FIG. 3 of embodiment 1 will be assigned the same reference numerals and explanation for repeated parts will be eliminated.

In FIG. 26, puncturing apparatus 111A has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a, which generates laser excitation light; and pedestal 114 as an puncturing opening, which projects from the surface of first case 112. Here, various menu buttons 113c such as puncturing and measurement are provided on the surface of first case 112a, and various operation buttons 113d are provided below display section 131 on second case 112b.

Figure 26A:
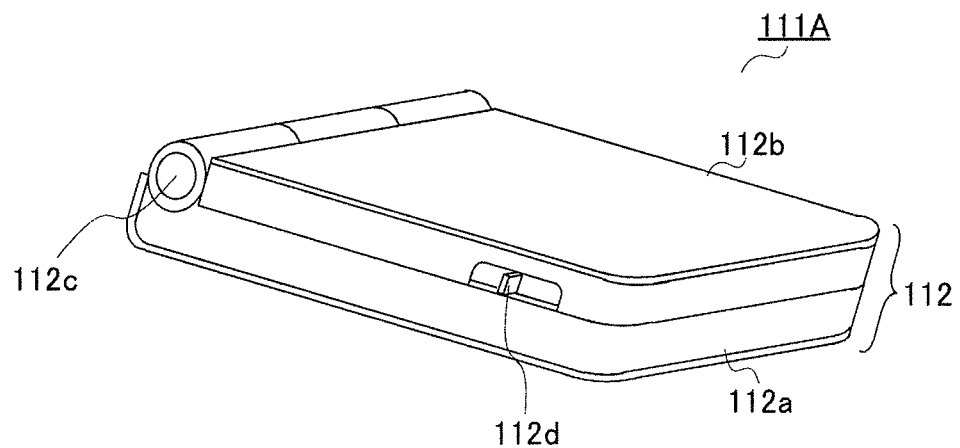
FIG. 26 is a perspective view showing a configuration of a puncturing apparatus according to embodiment 11 of the present invention.
Figure 26B:
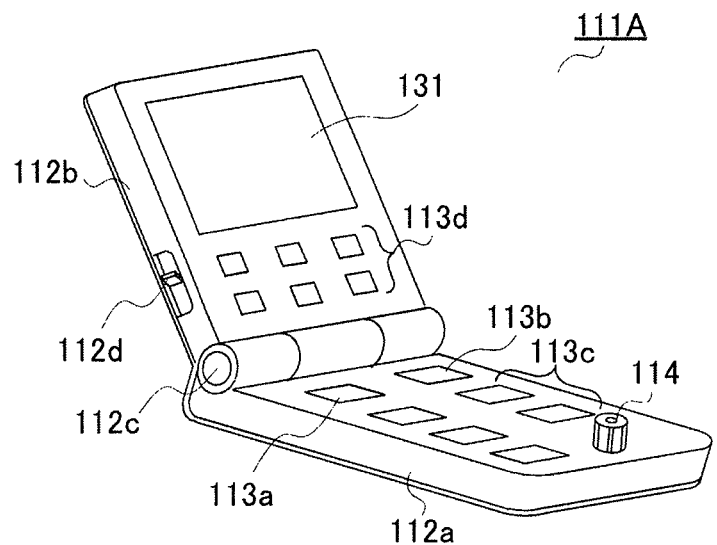

FIG. 26A shows a state where first case 112a and second case 112b are placed in the overlapping state via hinge part 112c. FIG. 26B shows a state where second case 112b is opened from first case 112a via hinge part 112c, so that first case 112a and second case 112c are placed in the non-overlapping state.

As shown in FIG. 26B, opening and closing switch 112d is provided in order to open second case 112b. Second case 112b can be released from the closed state and can be opened by operating opening and closing switch 112d. By this means, the puncturing starting mechanism is enabled. That is, opening and closing switch 112d functions as a releasing switch that releases first safety means 117.

In addition, opening and closing switch 112d can enable the puncturing starting mechanism (puncturing button 113a) by moving this opening and closing switch 112d to a predetermined position without the intention to open second case 112b. That is, even if second case 112b is open, the puncturing starting mechanism (puncturing button 113a) is not enabled if opening and closing switch 112b is not moved to the predetermined position.

FIG. 26B shows a state where second case 112b is open and pedestal 114 projects from the surface of first case 112a.

In this state, pedestal 114 is pressed, so that the puncturing starting mechanism configured by switch 114 (see FIG. 4) is enabled. In addition, laser emitting device 115 (see FIG. 2) is housed in first case 112a, and laser light 116a emitted from laser emitting device 115 penetrates pedestal 114 and punctures skin.

By pressing puncturing button 113 while the patient attaches skin 9 (not shown) of, for example, his/her finger to tip 114d of pedestal 114, laser light 115a is emitted, and a small amount of blood (not shown) exudes from skin 9.

In the overlapping state as shown in FIG. 26A, since puncturing apparatus 111A covers puncturing button with second case 112b, the press of puncturing button by wrong operation is prevented and the safety is ensured. In addition, since pedestal 114 irradiated with laser light 115a is covered with second case 112b, laser light 115a is not emitted outside, and therefore safety is assured.

Moreover, in the non-overlapping state as shown in FIG. 26B, puncturing button 113a is not enabled until switch 114b (see FIG. 3) is operated.

Here, in a state where first case 112a and second case 112b are open, pedestal 114, which is a part puncturing a finger and so forth, projects from the surface of case 112b. This provides an effect making it possible to ensure the distance between the condenser lens and the skin required to focus laser light and puncture the skin. In addition, it is possible to clarify the position to perform puncturing by projecting and emphasizing pedestal 114. Moreover, pressing this projecting pedestal 114 to the bottom allows pedestal 114 to have a function to initiate operation, and therefore, an effect of making pedestal 114 serve as a switch can be provided. For example, a micro switch may detect the press of this pedestal 114 to the bottom.

As described above, puncturing apparatus 111A of the present embodiment has the double safety means, so that laser light 115a is not emitted by mistake and a safe puncturing apparatus can be provided as with embodiment 1.

Moreover, first case 112a and second 112b are folded to make them in the overlapping state, so that the whole apparatus becomes compact, which is convenient for portable use.

(Embodiment 12)

Figure 27A:
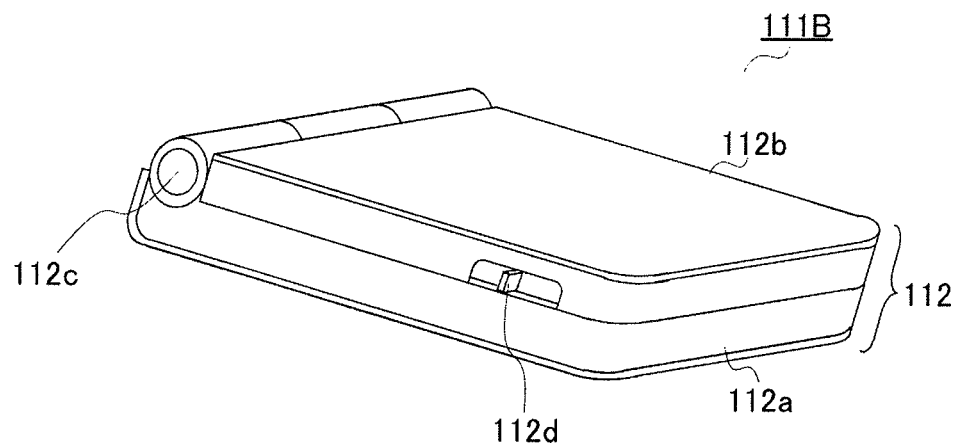
FIG. 27 is a perspective view showing a configuration of a puncturing apparatus according to embodiment 12 of the present invention.
Figure 27B:
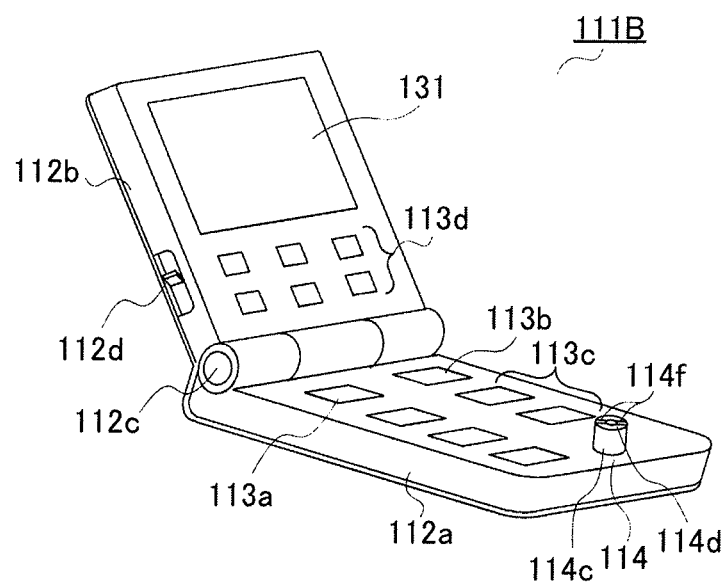

FIG. 27 is a perspective view showing a configuration of a puncturing apparatus according to embodiment 12. Here, the same components as in FIG. 26 will be assigned the same reference numerals and explanation for repeated parts will be eliminated.

In FIG. 27, puncturing apparatus 111B has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; and pedestal 114 as an puncturing opening that projects from the surface of first case 112a.

Skin detecting sensor 114f that detects contact with skin 9 (not shown) of the patient is provided at tip 114d of pedestal 114. Skin detecting sensor 114f is connected to control section 116 (see FIG. 3). In addition, pedestal 114 has black exterior surface 114c for antireflection and light shielding. Moreover, a darkness detecting sensor (not shown) that detects outside light is provided in first case 112a that houses the lower part of pedestal 114. The darkness detecting sensor is connected to control section 116 (see FIG. 3). This darkness detecting sensor detects change in the brightness when tip 114d of pedestal 114 is covered with skin 9 and so forth of the patient and the puncturing opening is shielded from light. Skin detecting sensor 114f can identify the presence or absence of contact with skin 9 of the patient based on change in electrical resistance, but cannot detect contact with a nonconductor. When tip 114d of pedestal 114 is shielded from light, the darkness detecting sensor can detect that.

As described above, puncturing apparatus 111B of the present embodiment has double safety means, so that laser light 115a is not emitted by mistake and a safe puncturing apparatus can be provided as with embodiment 11.

In addition, it is possible to shield outside light so as to prevent the darkness detecting means from operating erroneously by making pedestal 114 black or providing a shielding plate around pedestal 114. Moreover, it is possible to prevent puncturing light from leaking outside, so that safety can be ensured.

Furthermore, the puncturing starting mechanism is operated based on detection by the skin contact part (skin detecting sensor 114f) of pedestal 114 and detection by the darkness detecting sensor in pedestal 114, and therefore an effect of further improving safety is provided.

Here, although both skin detecting sensor 114f and the darkness detecting sensor are provided in the present embodiment, use of only one of skin detecting sensor 114f and the darkness detecting sensor may be applicable.

(Embodiment 13)

Figure 28A:
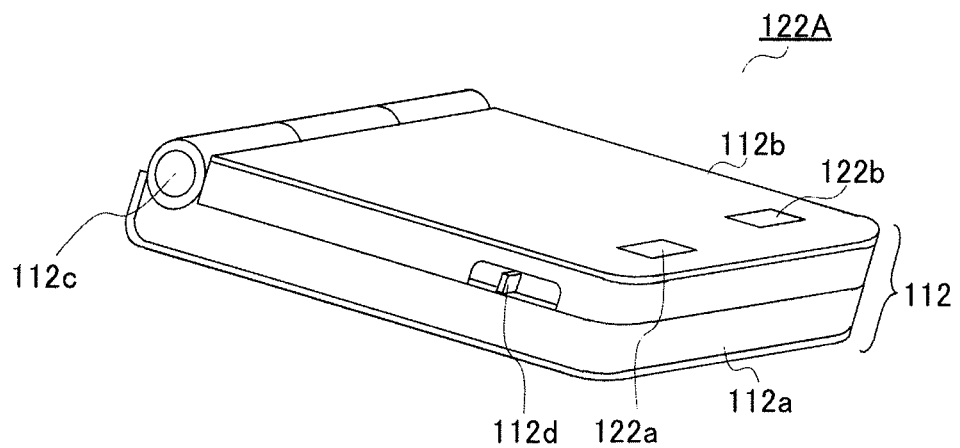
FIG. 28 is a perspective view showing a configuration of a puncturing apparatus according to embodiment 13 of the present invention.
Figure 28B:
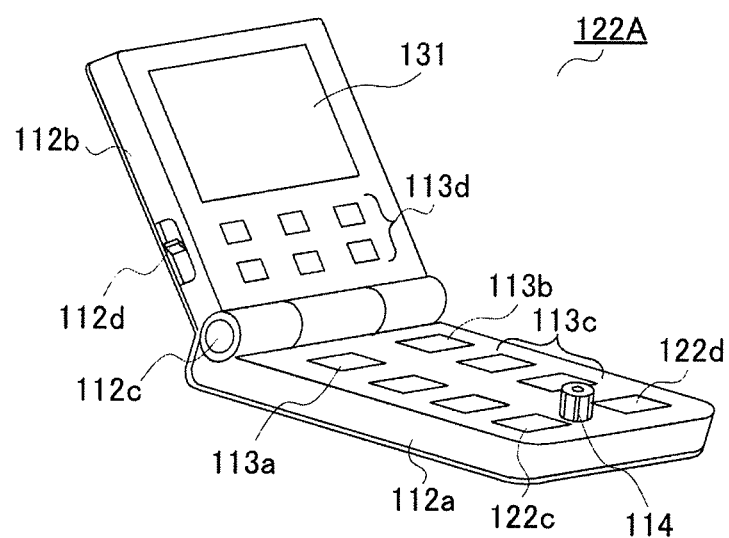

FIG. 28 is a perspective view showing a configuration of a puncturing apparatus according to embodiment 13. The same components as in FIG. 8 and FIG. 26 in the above-described embodiment 3 will be assigned the same reference numerals and explanation for repeated parts will be eliminated.

In FIG. 28, puncturing apparatus 122A has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; pedestal 114 as an puncturing opening that projects from the surface of first case 112a; safety releasing buttons 122a and 122b provided on the upper side of second case 112b; and safety releasing buttons 122c and 122d provided on the upper side of first case 112a. In addition, laser emitting device 115 (see FIG. 3) is housed in first case 112a, laser light 115a emitted from laser emitting device 115 penetrates pedestal 114 and punctures skin.

Safety releasing buttons 122a to 122d are connected to control section 116 (see FIG. 3), and control section 116 detects press the press of safety releasing buttons 122a to 122d.

Safety releasing buttons 122a and 122b enables the puncturing starting mechanism that releases first safety means 117A used in the overlapping state. Meanwhile, safety releasing buttons 122c and 122d serve to release second safety button 118A used in the non-overlapping state. First safety means 117A (not shown) of the present embodiment further includes a safety means composed of safety releasing buttons 122a and 122b, in addition to first safety means 117 as shown in FIG. 3 of the above-described embodiment 1. In the same way, second safety means 118A (not shown) further includes a safety means composed of safety releasing buttons 122c and 122d, in addition to second safety means 118 as shown in FIG. 3.

As first safety means 117A used in the overlapping state, two safety releasing buttons 122a and 122b are mounted on the upper side of second case 112b. These safety releasing buttons 122a and 122b are pressed within a predetermined time period and in a predetermined press order, so that puncturing operation can be started.

As second safety means 118A used in the non-overlapping state, two safety releasing buttons 122c and 122d are mounted on the upper side of first case 112a. These safety releasing buttons 122c and 122d are pressed within a predetermined time period and in a predetermined pressing order, so that start of puncturing operation is released.

As described above, puncturing apparatus 122A has first safety means 117A and second safety means 118A, so that security can be ensured and safety can be further improved as with embodiment 3.

That is, puncturing apparatus 122A has a mechanism that adapts to both the open state and the closed state of the opening and closing parts, and for the closed state, the releasing mechanism operates on the first safety means and for the open state, the releasing mechanism operates on the second releasing mechanism. Moreover, an effect of ensuring security of safety releasing operation is provided by: providing at least two buttons; storing the order to press each button in advance and setting so as not to operate unless the button is pressed in the stored order; and initially setting the order to press the buttons in the designated state.

Here, although the present embodiment further employs a safety means composed of safety releasing buttons 123a and 123b, in addition to first safety means 117 as shown in FIG. 3 of the above-described embodiment 1, and also further employs a safety means composed of safety releasing buttons 123c to 123f, in addition to safety means 118 as shown in FIG. 3, either the safety means composed of safety releasing buttons 123a and 123b or the safety means composed of safety releasing buttons 123c to 123f may be employed independently.

Here, although the present embodiment has a configuration having the first safety means used in the overlapping state and the second safety means used in the non-overlapping state, another configuration having only one of the safety means is applicable.

In addition, the number, the mounting positions and the types of safety releasing buttons 123a to 123f are not limited. Moreover, the operational sequence of safety releasing buttons 123a to 123f can be arbitrarily set.

(Embodiment 14)

Figure 29A:
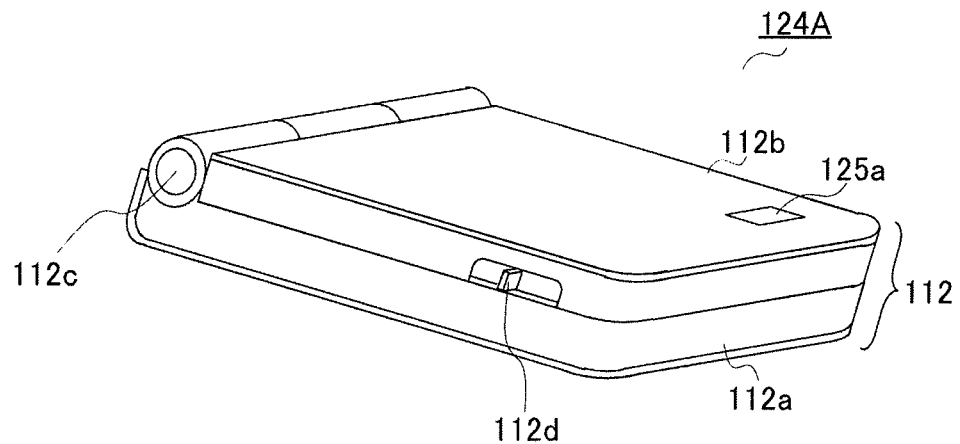
FIG. 29 is a perspective view showing a configuration of a puncturing apparatus according to embodiment 14 of the present invention.
Figure 29B:
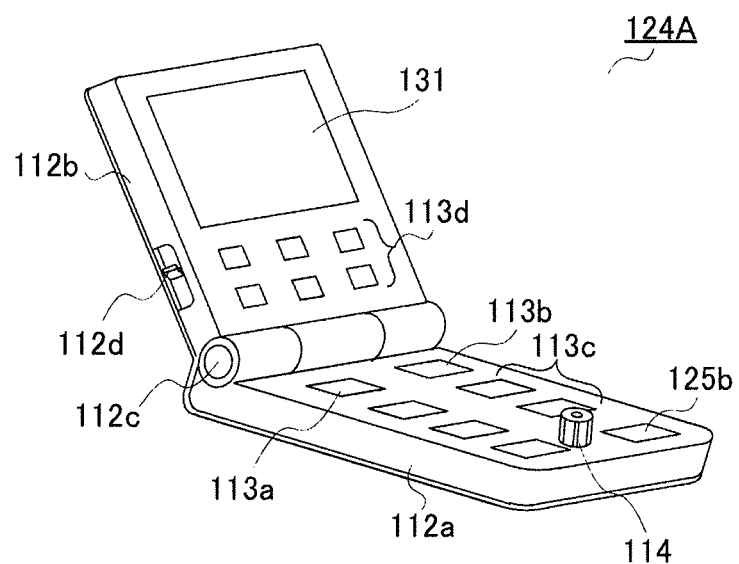

FIG. 29 is a perspective view showing a configuration of a puncturing apparatus according to embodiment 14 of the present invention. FIG. 29A shows a state where first case 112a and second case 112b are placed in the overlapping state via hinge part 112c, and FIG. 29B shows a state where second case 112b is opened from first case 112a via hinge part 112c, so that first case 112a and second case 112b are placed in the non-overlapping state. The same components as in FIG. 9 and FIG. 26 will be assigned the same reference numerals and explanation for repeated parts will be eliminated.

In FIG. 29, puncturing apparatus 124A has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; pedestal 114 as an puncturing opening that projects from the surface of first case 112a; fingerprint identifying section 125a mounted on the upper side of second case 112b; and fingerprint identifying section 125b mounted on the upper side of first case 112a.

Fingerprint identifying sections 125a and 125b are connected to control section 116 (see FIG. 116), and control section 116 identifies the fingerprint detected by fingerprint identifying sections 125a and 125b.

Fingerprint identifying section 125a constitutes a releasing mechanism for the first safety means used in the overlapping state, and fingerprint identifying section 125b constitutes a releasing mechanism for the second safety means used in the non-overlapping state. First safety means 117B of the present embodiment further includes a safety means configured by fingerprint identifying section 125a, in addition to first safety means 117 of embodiment 1 as shown in FIG. 3 of embodiment 1. Meanwhile, second safety means 118B of the present embodiment further includes a safety means configured by fingerprint identifying section 125b, in addition to second safety means 118 shown in FIG. 3.

Fingerprint identifying sections 125a and 125b identify the detected fingerprint and outputs the identification result to control section 116 (see FIG. 3).

Control section 116 judges qualification of the user, based on correspondence between the fingerprint pattern identified by fingerprint identifying sections 125a and 125b and the fingerprint of the patient registered in advance.

As described above, puncturing apparatus 124A further includes fingerprint identifying sections 125a and 125b, so that safety can be further improved as with embodiment 4, from another viewpoint which is personal identification.

That is, puncturing apparatus 124A has the mechanism that can adapts to both the closed state and open state of the opening and closing parts, and for the closed state, the mechanism serves as a releasing mechanism for the first safety means and for the open state, the mechanism serves as releasing mechanism for the second safety means. An effect of ensuring security of safety releasing operation is provided by recognizing the finger print of the user in advance and allowing to operate after the fingerprint authentication system authenticates the user's fingerprint.

Here, although the present embodiment has a configuration including both fingerprint identifying section 125a used in the overlapping state and fingerprint identifying section 125b used in the non-overlapping state, another configuration having only one of the fingerprint identifying sections is applicable.

(Embodiment 15)

Figure 30A:
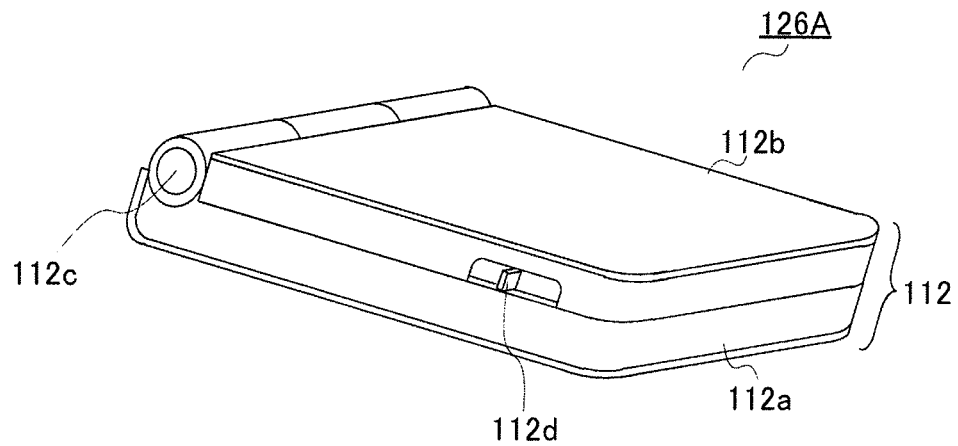
FIG. 30 is a perspective view showing a configuration of a puncturing apparatus according to embodiment 15 of the present invention.

FIG. 30 is a perspective view showing a configuration of a puncturing apparatus according to embodiment 15 of the present invention, and shows a state where second case 112b is opened from first case 112a via hinge part 112c, so that first case 112a and second case 112b are placed in the non-overlapping state. The same components as in FIG. 10 and FIG. 26 will be assigned the same reference numerals and explanation for repeated parts will be eliminated.

In FIG. 30, puncturing apparatus 126A has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; pedestal 114 as an puncturing opening that projects from the surface of first case 112a; and knob 127e provided on the upper side of first case 112a.

Knob 127e is connected to control section 116 (see FIG. 3), and control section 116 detects the rotating operation of knob 127e.

Knob 127e constitutes a releasing mechanism for the second safety means used in the non-overlapping state.

As second safety means 118C used in the non-overlapping state, pointing device 127 is provided on the upper side of first case 112a. This pointing device 127 is operated in a predetermined operational sequence, so that the puncturing starting mechanism is released.

As described above, puncturing apparatus 126A has second safety means 118C, so that security can be ensured and also safety can be further improved as with embodiment 9.

Figure 30B:
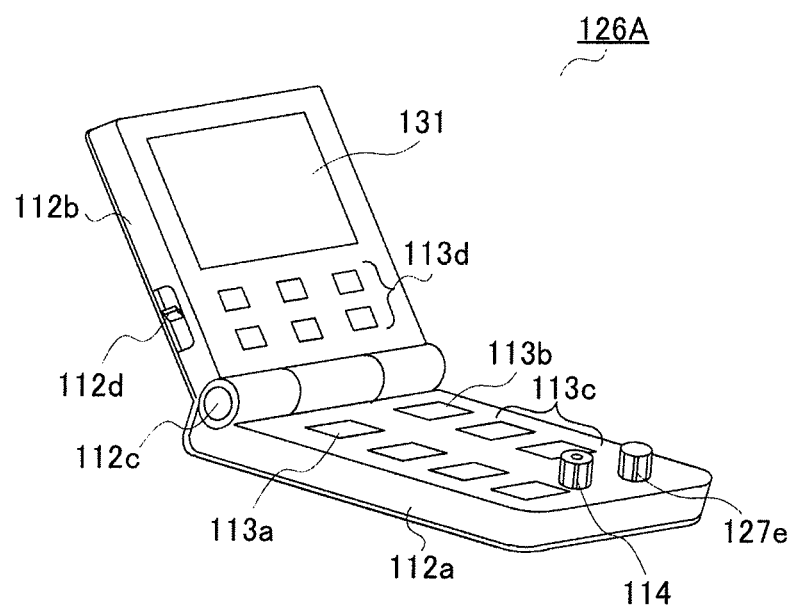

That is, puncturing apparatus 126A has an input mechanism that can be operated in the open state of the opening and closing parts (the state as shown in FIG. 30B) and releases the releasing mechanism of second safety means 118C by operating this input mechanism, so that an effect that ensures the personal security can be obtained. For example, knob 127e which is the input mechanism protrudes in the state where the opening and closing parts are open (the state as shown in FIG. 30B) and steps of puncturing operation are decided, an effect of improving safety can be obtained with simple operation.

In this case, the input mechanism is configured to serve as a means for setting the level of power of the puncturing mechanism and also for inputting information (date, user ID, etc.), so that an effect that performs two setting by one operation can be obtained.

(Embodiment 16)

FIG. 31 is a perspective view showing a configuration of a puncturing apparatus according to embodiment 16 of the present invention. The same components as in FIG. 15 and FIG. 26 will be assigned the same reference numerals and explanation for repeated parts will be eliminated.

In FIG. 31, puncturing apparatus 128A has a configuration including: housing 112 composed of first case 112a, second case 112b and hinge part 112c; an inner cover 129 provided between first case 112a and second case 112b; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; and puncturing opening 130 that projects from the surface of first case 112a. Laser emitting device 115 (see FIG. 3) is housed in first case 112a, and laser light 115a emitted from laser emitting device 115 penetrates puncturing opening 130 and punctures skin.

Even if puncturing is performed by operating puncturing button 113a, inner cover 129 blocks the puncturing through puncturing opening 130 provided on first case 112a.

Figure 31A:
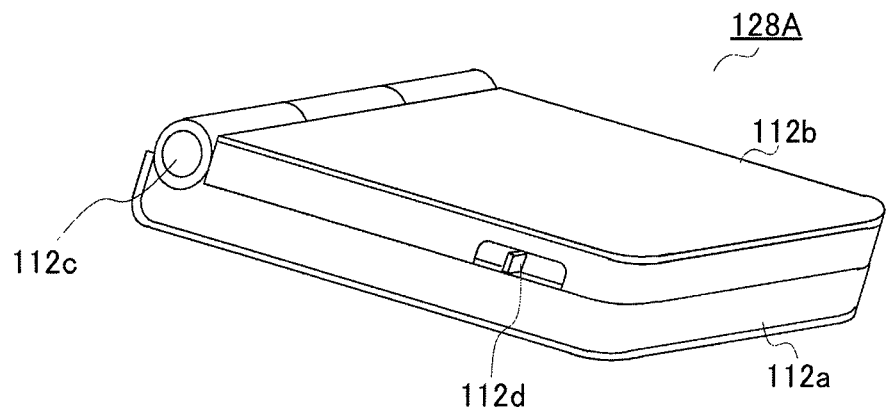
FIG. 31 is a perspective view showing a configuration of a puncturing apparatus according to embodiment 16 of the present invention.
Figure 31B:
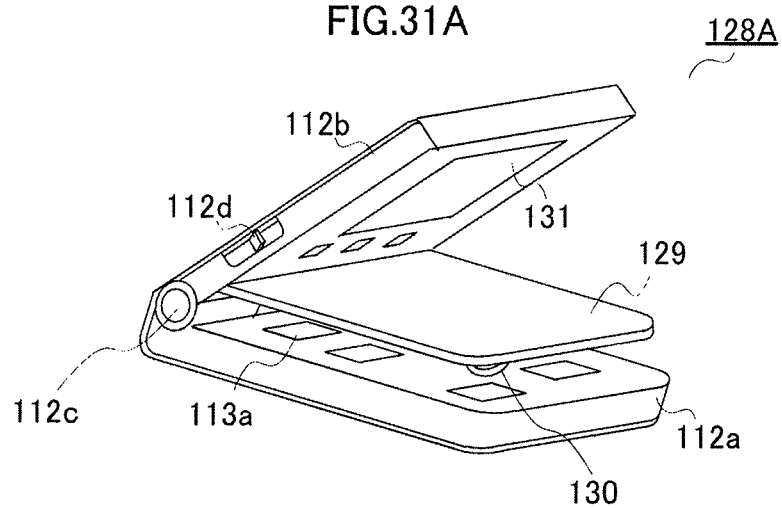
Figure 31C:
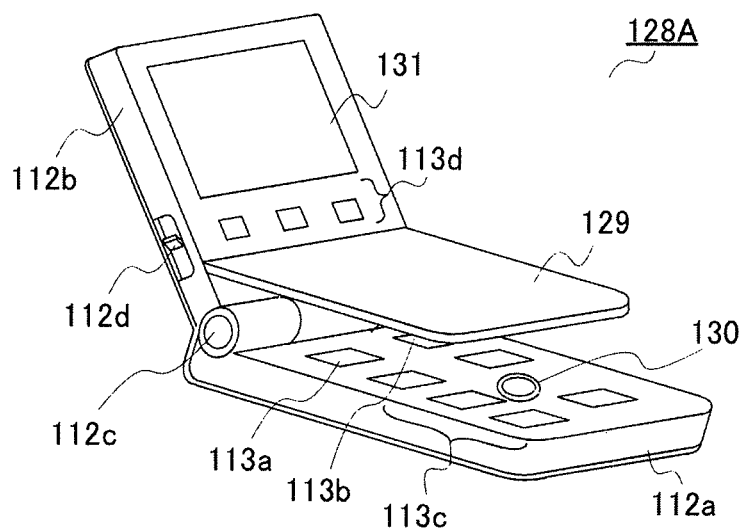

FIG. 31A shows a state where first case 112a and second case 112b are closed via hinge part 1 12c; FIG. 31B shows a state where second case 112b is open at the first level, from first case 112a to the position; and FIG. 31C shows a state where second case 112b is open at the second level, from first case 112a to the puncturing possible position, that is, second case 112 is open in the position at the second step.

In the state where second case 112 is open to the position in the first step as shown in FIG. 31B, inner cover 129 is located between first case 112a in which puncturing opening 130 is provided and second case 112b. Then, puncturing is performed in this state. At this time, inner cover 129 serves as first safety means 117C (not shown) so as not to leak laser light 115a outside.

In addition, more preferably, the material for the part of inner cover 129 where laser light 115a is received is a light-absorbing member.

In the state where second case 112b is open in the position at the second level as shown in FIG. 31, it is possible to view the display of display section 131 provided in second case 112b.

As described above, according to the present embodiment, puncturing apparatus 128A has inner cover 129 between first case 112a and second case 112b, so that it is possible to prevent laser puncturing light from leaking outside in the open state and risk in puncturing can be physically eliminated.

(Embodiment 17)

FIG. 32 is a perspective view showing a configuration of a puncturing apparatus according to embodiment 17 of the present invention. The same components as in FIG. 16 and FIG. 26 will be assigned the same reference numerals and explanation for repeated parts will be eliminated.

In FIG. 32, puncturing apparatus 132A has a configuration including: housing 112 composed of first case 112a, second case 112b and hinge part 112c; opening and closing switch 112d for first case 112a and second case 112b, which is provided on the side surface of second case 112b; display section 131 provided in second case 112b; puncturing button 113a provided on the surface of first case 112a; capacitor charging button 113b provided on the surface of first case 112a; and puncturing opening 130 that projects from the surface of first case 112a. Laser emitting device 115 (see FIG. 3) is housed in first case 112a, and laser light 115a emitted from laser emitting device 115 penetrates puncturing opening 130 and punctures skin.

Puncturing apparatus 132A has a two-step opening and closing mechanism that locks once opening and closing of first case 112a and second case 112b in a position between the overlapping state and the second overlapping state. Here, puncturing apparatus 132A allows a puncturing releasing means to operate in the locked position. The locked position provided by the two-step opening and closing mechanism is the position in which second case 112b that faces puncturing opening 130 provided on first case 112a blocks laser light when puncturing is performed by operating puncturing button 113a.

Figure 32A:
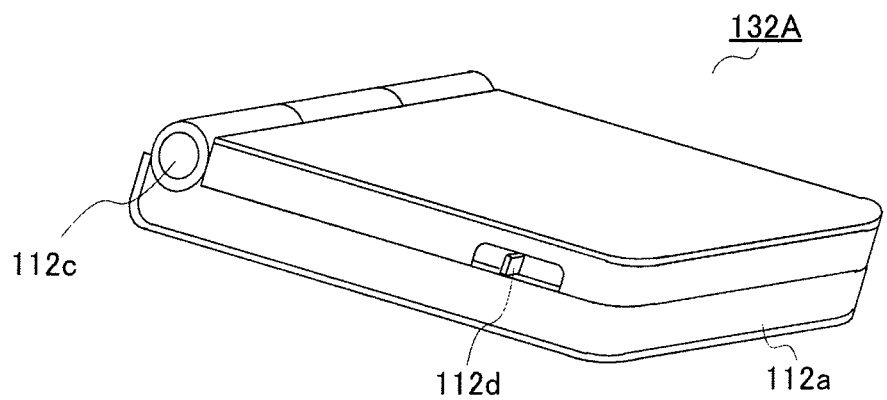
FIG. 32 is a perspective view showing a configuration of a puncturing apparatus according to embodiment 17 of the present invention.
Figure 32B:
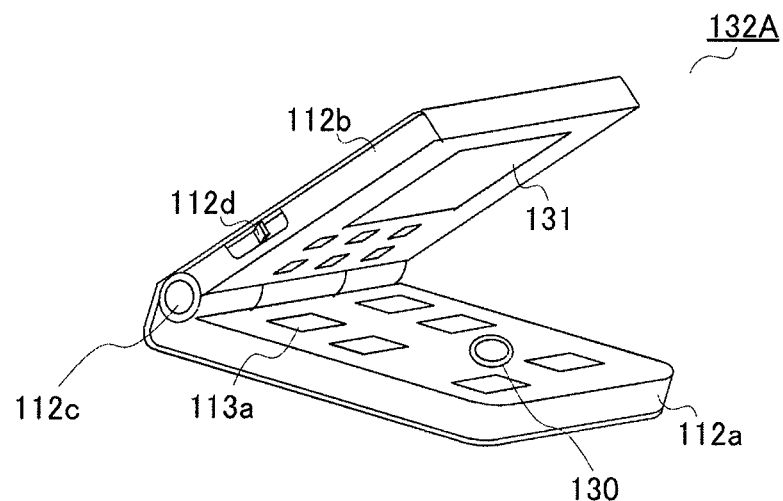

FIG. 32A shows a state where first case 112a and second case 112b are closed via hinge part 112c; FIG. 32B shows a state where second case 112b is open from first case 112a to the position in the first step, which is the puncturing position; and FIG. 32C shows a state where second case 112b is open from first case 112a to the position in the second step via hinge part 112c.

Puncturing apparatus 132A performs puncturing in the state where second case 112b is open in the position at the first level as shown in FIG. 32B. That is, puncturing apparatus 132A can perform puncturing in the position where puncturing opening 130 is covered with second case 112b as shown in FIG. 32B. In addition, puncturing operation by puncturing apparatus 132A is prohibited in the state where second case 112b is open in the position at the second step as shown in FIG. 32C. For example, a mechanical switch provided in hinge part 112c detects that puncturing apparatus 132A is in the state shown in FIG. 32B and FIG. 32C.

In the present embodiment, second case 112b itself serves as first safety means 117D (not shown) so as not to leak laser light 115a outside.

Figure 32C:
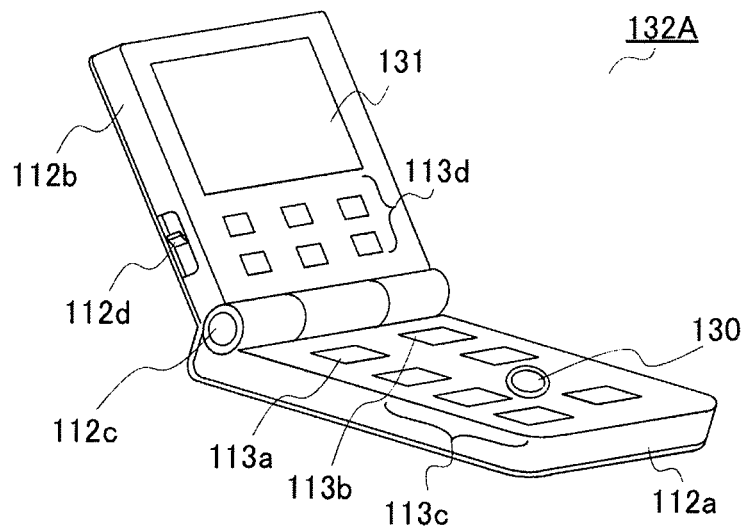

FIG. 32C shows the non-overlapping state in the second step with a large open angle. In this state, display of measurement data and so forth can be viewed by display section 131 provided in second case 112b. Here, this display section 131 can be efficiently used as display section 131 of blood test apparatus 141 of the above-described embodiment 10.

As described above, according to the present embodiment, puncturing apparatus 132A has the two-step opening and closing mechanism that locks once opening and closing of first case 112a and second case 112b between the overlapping state and the non-overlapping state, and performs the puncturing releasing means when first case 112a and second case 112b lock in the opening and closing position at the first level.

Therefore, it is possible to prevent laser puncturing light from leaking outside even if first case 112a and second case 112b are in the non-overlapping state, so that risk in puncturing can be physically eliminated. For example, in the case of a blood test apparatus including a puncturing mechanism using laser light and so forth and a bioanalysis section, an effect of eliminating risk in puncturing when laser light and so forth is used can be obtained by having a mechanism that can open and close a top cover and a base and having a structure where the top cover folds in order to prevent light from leaking outside when the puncturing mechanism operate erroneously in the open state.

In addition, in the opening state at the second level, the display on display section 131 provided in second case 112b can be viewed. In this case, large display section 131 can fill the entire case 112b, so that it is possible to provide a screen, which is easily viewable to the patient with poor eyesight.

(Embodiment 18)

FIG. 33 is a perspective view showing a configuration of a puncturing apparatus according to embodiment 18 of the present invention. The same components as in FIG. 26 will be assigned the same reference numerals and explanation for repeated parts will be eliminated.

In FIG. 32, puncturing apparatus 134 has a configuration including: first case 134a having a rectangular solid shape that forms the lower part of the body; second case 134b as a lid part that forms the upper part of the body; hinge part 134c; opening and closing switch 134d for first case 134a and second case 134b, which is provided on the side surface of second case 134b; display section 131 provided on the surface of first case 134a; various operation buttons provided below display section 131; puncturing button 113a provided on the upper surface of first case 134a; capacitor charging button 113b provided on the upper surface of first case 134a; puncturing opening 130 that projects from the upper surface of first case 134a; and various menu buttons 113c for puncturing, measurement and so forth provided on the upper surface of first case 134a. Laser emitting device 115 (see FIG. 3) is housed in first case 134a, and laser light 115 emitted from laser emitting device 115 penetrates puncturing opening 130 and punctures skin.

Figure 33A:
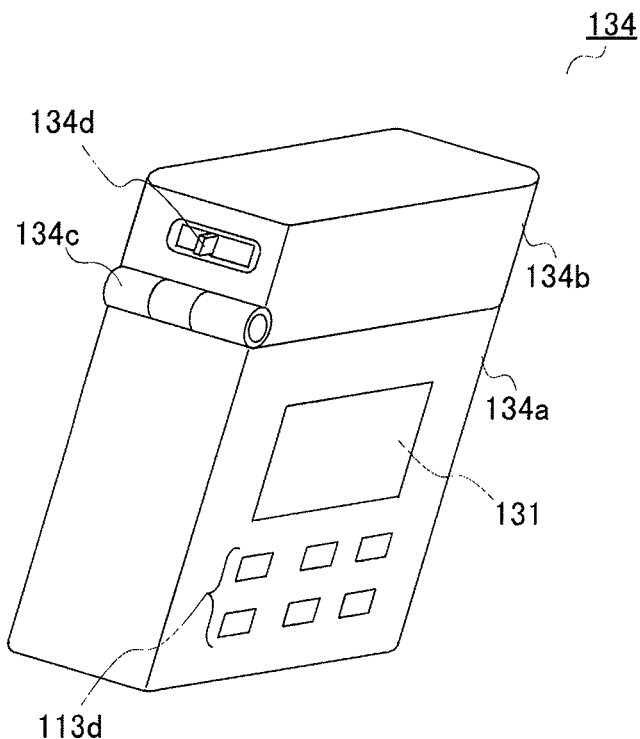
FIG. 33 is a perspective view showing a configuration of a puncturing apparatus according to embodiment 18 of the present invention.
Figure 33B:
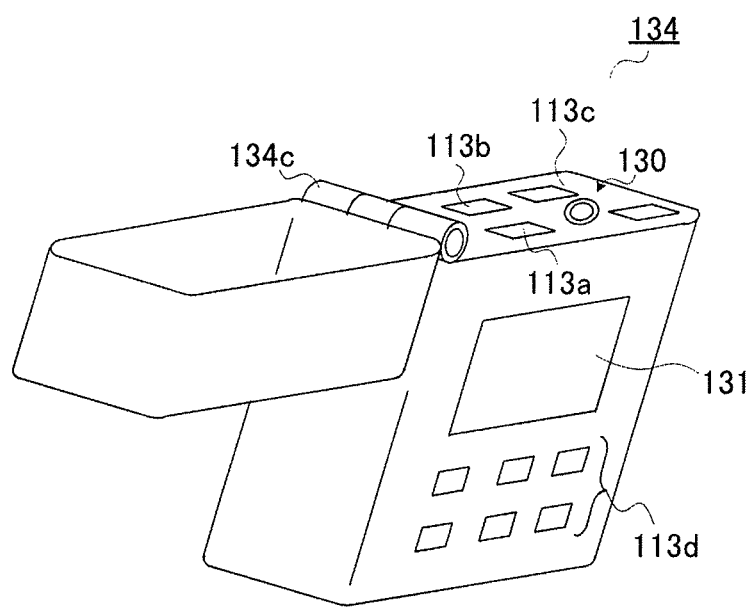

FIG. 33A show a state where first case 134a and second case 134b are placed in the overlapping state via hinge part 134c and FIG. 33B shows a state where second case 134b is opened from first case 134a via hinge part 134c, so that second case 134b and first case 134a are placed in the non-overlapping state.

As shown in FIG. 33B, opening and closing switch 134d is released in order to open second case 134b. Opening and closing switch 134d has a function to enable the puncturing starting mechanism of first safety means 117 in the state where second case 134 is closed.

As shown in FIG. 33B, when opening and closing switch 134d is released and second case 134 is opened, so that the non-overlapping state is made, puncturing button 113a, capacitor charging button 113b and puncturing opening 130 appear on the upper side of first case 134a.

In the overlapping state shown in FIG. 33A, second case 134b covers puncturing button 113a and puncturing opening 130, so that puncturing button 113a is not pressed by erroneous operation and therefore puncturing apparatus 134 can assure safety.

As described above, in puncturing apparatus 134 of the present invention, second case 134b serves as the lid of first case 134 and second case 134b as the lid is mounted to shield the puncturing section. Puncturing apparatus 134 has double safety means as with the puncturing apparatus according to each embodiment described above, so that it is not possible to perform puncturing until first safety means 117 is released. By this means, laser light 115a is not emitted erroneously, so that a safe puncturing apparatus can be provided.

In addition, first case 134a and second case 134b are placed in the overlapping state, that is the overlapping state is made, so that the apparatus becomes compact, which is convenient for portable use.

Moreover, puncturing apparatus 134 of the present embodiment has a rectangular solid shape such that second case 134b serves as the lid of first case 134a, so that display section 131 can be always displayed on the surface of first case 134a. The measurement result and so forth can be checked at any time, so that convenience can be improved.

(Embodiment 19)

In embodiment 19, the relationship between the laser section and the puncturing position will be described.

In a case where a puncturing apparatus adopts a laser emitting device as a puncturing means, the relationship between the laser section and the puncturing position is as follows.

There are two types of laser section: one is a vertically long type; and the other is a short type. First, the type of long vertical laser section will be described.

Figure 34:
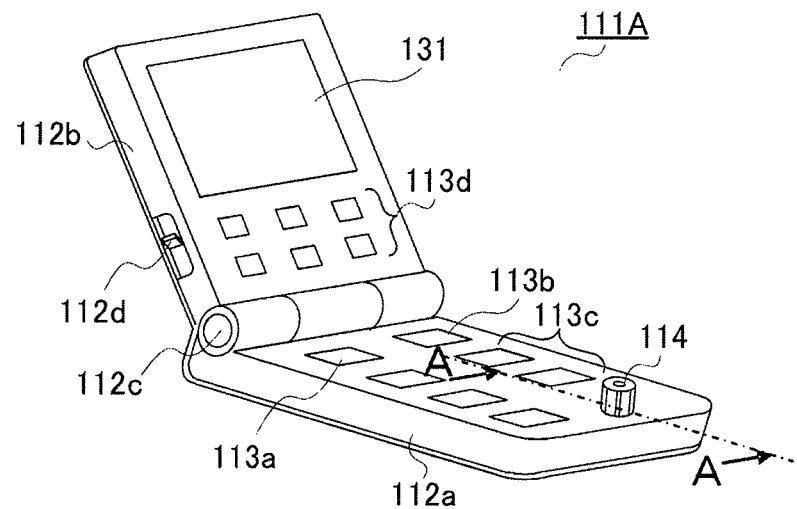
FIG. 34 is a perspective view showing a configuration of a puncturing apparatus according to embodiment 19 of the present invention.
Figure 35:
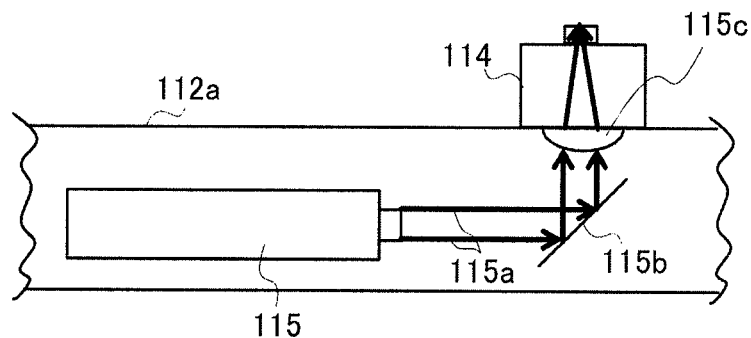
FIG. 35 is a cross sectional view along the line A-A in FIG. 34.

FIG. 34 is a perspective view showing a configuration of a puncturing apparatus according to embodiment 19 of the present invention. FIG. 35 is a cross sectional view along the line A-A of FIG. 34. The same components as in FIG. 24 and FIG. 26 will be assigned the same reference numerals and explanation for repeated parts will be eliminated.

Although the present embodiment is an example applied to puncturing apparatus 111A as shown in FIG. 26, the present embodiment may be applied to another embodiment. For example, the present embodiment may be applied to embodiment 1 as shown in FIG. 2 to FIG. 5. In this case, FIG. 35 schematically shows FIG. 4

As shown in FIG. 35, in a case of laser emitting apparatus 115 of the type with long vertical laser section, reflecting mirror 115b that bends incident laser light 115a at 90 degrees, so that the laser emitting direction for puncturing is changed. Laser light 115a changes its traveling direction at 90 degrees by reflecting mirror 115b, passes through lens 115c and punctures skin 9. By this means, laser light 115a emitted from laser emitting device 115 can be set so as to accurately focus on the vicinity of the surface of skin 9.

Next, the type of short laser section will be described.

Figure 36:
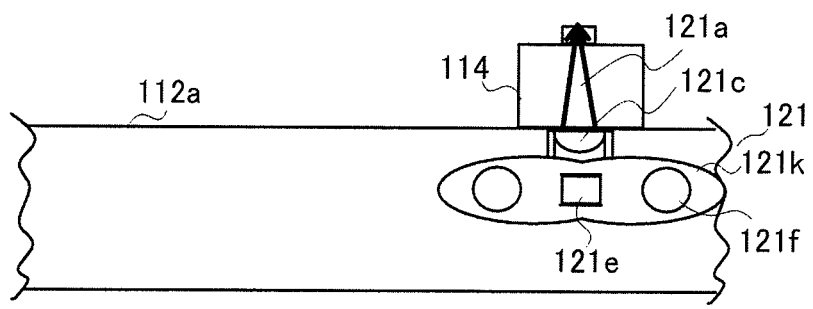
FIG. 36 is a cross sectional view along the line A-A in FIG. 34.
Figure 37A:
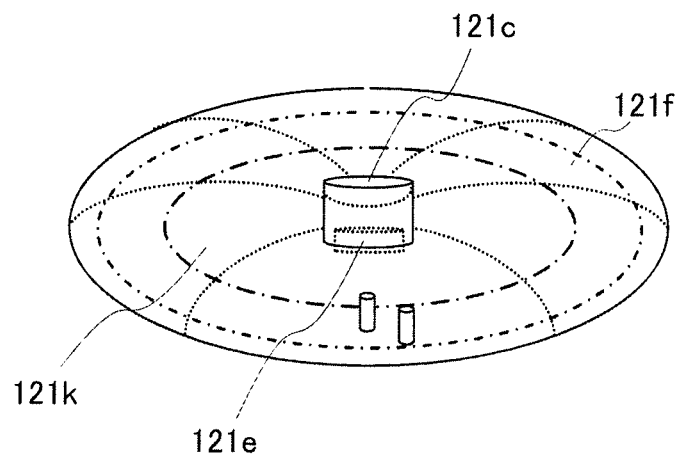
FIG. 37 is an enlarged view of primary parts of the laser emitting device of FIG. 36.
Figure 37B:
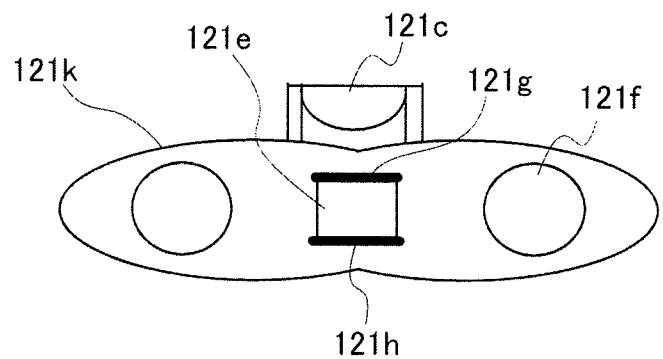

FIG. 36 is a cross sectional view along the line A-A of FIG. 34. In addition, FIG. 37 is an enlarged view showing laser emitting device 121 and its primary parts of FIG. 36, FIG. 37A is a perspective view of FIG. 37, and FIG. 37B is a cross sectional view of FIG. 37. FIG. 36 and FIG. 37 schematically show embodiment 2 of FIG. 6. The same components as in FIG. 6 will be assigned the same reference numerals and explanation for repeated parts will be eliminated.

As shown in FIG. 36 and FIG. 37, laser emitting device 121 having the short type of laser section has laser crystal 121e, which is a laser generating rod and a flash light source in lens-barrel 121. As shown in FIG. 37A, flash light source 121f encloses the whole circumference of laser crystal 121e. Partially transmitting mirror 212g is mounted on lens 121c side, and total reflecting mirror 121h is mounted on the opposite side. By this configuration, the dimension of laser light 121a in the emitting direction can be extremely shorten, so that the thickness of laser emitting device 121 can be reduced.

In addition, laser crystal 121e is enclosed by flash light source 121f, so that the efficiency of flash light source 121f is more improved than laser emitting device 115 of embodiment 1.

Here, excitation light of a semiconductor laser may be used instead of flash light source 121f.

The above description is illustration of preferred embodiments of the present invention and the scope of the invention is not limited to this.

For example, although laser emitting device 115 is used as a puncturing means in each of the above-described embodiments, the present invention is not limited to this and a needle puncturing device that performs puncturing using a puncturing needle may be employed as a puncturing means.

Furthermore, although the names "puncturing apparatus" and "blood test apparatus" are used in the present embodiment for convenience of explanation, it goes without saying that the name of the apparatus may be a "test apparatus", and the name of the method may be a "method for controlling a puncturing apparatus" and so forth.

Moreover, for each component constituting the puncturing apparatus and the blood test apparatus, such as the kind of laser, the number and the connection method thereof are not limited.

The present invention claims priority based on Japanese Patent Application No. 2007-198375, filed on Jul. 31, 2007. The disclosure including the specification and drawings as filed, is incorporated herein by reference in its entirety.

INDUSTRIAL APPLICABILITY

The puncturing apparatus and the blood test apparatus according to the present invention have improved safety by preventing erroneous operation and are applicable to blood test apparatuses used in, for example, the medical field. Moreover, the present invention is preferably applicable to the blood test apparatus that punctures skin by the puncturing means such as the laser emitting device, samples blood exuding from skin and analyzes components of the blood.

The invention claimed is:

1. A puncturing apparatus comprising:
a housing having a first case and a second case, the housing configured to move at least one of the first case and the second case so that the cases are in an overlapping state in which the first case and the second case overlap one another, or are in a non-overlapping state;
a puncturer received in the housing, the puncturer configured to perform puncturing through a puncturing opening;
a puncture starting mechanism having a puncturing button, the puncture starting mechanism configured to activate the puncturer;
a first safety section configured to prevent exposure of at least one of the puncturing opening and the puncturing button upon movement of the first case and the second case to the overlapping state; and
a second safety section configured to disable operation of the puncture starting mechanism in the non-overlapping state of the first case and the second case,
wherein the second safety section is a pedestal having the puncturing opening, the pedestal being provided in one of the first case and the second case, and being disposed between the first case and the second case in the overlapping state, and
the pedestal is subjected to being pressed by the first case and the second case in the overlapping state so as to cover the puncturing opening with the first case or the second case, and is released from being pressed in the non-overlapping state so as to disable the operation of the puncture starting mechanism.

2. The puncturing apparatus according to claim 1, wherein the puncturer comprises a laser emitting device that punctures skin with laser light without contact.

3. The puncturing apparatus according to claim 1, wherein the puncturer comprises a needle puncturing device that punctures skin with a puncture needle.

4. The puncturing apparatus according to claim 1, wherein:
the first safety section comprises a hinge at a connection of an end of the first case and an end of the second case; and
the first case and the second case are opened and closed via the hinge.

5. The puncturing apparatus according to claim 1, wherein:
the first safety section comprises a slide on each side surface of the first case and the second case; and
the first case and the second case are slidably opened and closed through the slide.

6. The puncturing apparatus according to claim 1, wherein:
the first safety section comprises an axis at a connecting point of an end of the first case and the second case; and
the first case and the second case are pivotally opened and closed by pivoting about the axis.

7. The puncturing apparatus according to claim 1, wherein:
the second safety section is provided with a skin detecting sensor at a tip of the pedestal; and
operation of the puncture starting mechanism is enabled when the skin detecting sensor detects skin.

8. The puncturing apparatus according to claim 1, wherein:
the second safety section comprises a light receiving sensor inside the pedestal; and
operation of the puncture starting mechanism is enabled when an output of the light receiving sensor is changed.

9. The puncturing apparatus according to claim 1, wherein the second safety section is an operator that can perform a predetermined operation; and enables the puncture starting mechanism when the operator performs the predetermined operation.

10. The puncturing apparatus according to claim 9, wherein the operator inputs a pressing order of a plurality of buttons as operation information.

11. The puncturing apparatus according to claim 9, wherein the operator inputs, as operation information, one of rotation of a knob registered in advance; operation of a pointing device registered in advance; rotation of a volume registered in advance; operation of a trackball registered in advance; and operation of a dip switch registered in advance.

12. The puncturing apparatus according to claim 1, wherein:
the second safety section is a fingerprint identifier that identifies a pre-stored fingerprint; and
the puncture starting mechanism is enabled when the fingerprint identifier identifies the pre-stored fingerprint.

13. The puncturing apparatus according to claim 1, further comprising a multiple-stage opening and closing mechanism configured to lock opening and closing operation of the first case and the second case between the overlapping state and the non-overlapping state,
wherein the puncture starting mechanism is enabled when the multiple-stage opening and closing mechanism locks the opening and closing operation between the overlapping state and the non-overlapping state.

14. The puncturing apparatus according to claim 13, wherein a locked position by the multiple stage opening and closing mechanism is a position where puncturing from the puncturing opening provided in the first case is blocked by the second case facing the first case.

15. The puncturing apparatus according to claim 1, further comprising an inner cover between the first case and the second case,
wherein the inner cover blocks puncturing from the puncturing opening provided in the housing.

16. The puncturing apparatus according to claim 15, wherein the inner cover is provided in one of the first case and the second case.

17. The puncturing apparatus according to claim 15, wherein the inner cover is provided separately from the first case and the second case.

18. A blood test apparatus comprising:
a puncturing apparatus that punctures skin and tests components of blood exuding from the skin by puncturing,
wherein the puncturing apparatus comprises a puncturing apparatus according to claim 1.

19. The blood test apparatus according to claim 18, further comprising a negative pressure section that applies a negative pressure to a vicinity of the skin punctured by the puncturing apparatus.

20. The puncturing apparatus according to claim 1, wherein the puncturing opening is provided on a main surface of the first case which faces the second case in the overlapping state of the first case and the second case.

21. The puncturing apparatus according to claim 1, wherein the pedestal is distinct from the puncturing button.

* * * * *